(12) United States Patent
Egholm et al.

(10) Patent No.: US 6,316,230 B1
(45) Date of Patent: Nov. 13, 2001

(54) POLYMERASE EXTENSION AT 3' TERMINUS OF PNA-DNA CHIMERA

(75) Inventors: Michael Egholm, Wayland; Caifu Chen, Brookline, both of MA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/373,845

(22) Filed: Aug. 13, 1999

(51) Int. Cl.⁷ .............................. C12Q 1/68; C12P 19/34; C07H 19/00; C07H 21/00; C07H 21/02
(52) U.S. Cl. .................. 435/91.1; 435/6; 435/91.2; 536/22.1; 536/23.1; 536/24.3; 536/24.33; 536/25.3; 536/25.32; 536/25.6
(58) Field of Search .............. 435/6, 91.1, 91.2; 536/22.1, 23.1, 24.3, 24.33, 25.3, 25.32, 25.6

(56) References Cited

U.S. PATENT DOCUMENTS

| | | | |
|---|---|---|---|
| 5,332,666 | * | 7/1994 | Prober et al. ..................... 435/91.5 |
| 6,063,571 | * | 5/2000 | Uhlmann et al. ..................... 435/6 |

FOREIGN PATENT DOCUMENTS

| | | |
|---|---|---|
| 0 672 677 | 9/1995 | (EP) . |
| 0 829 542 | 3/1998 | (EP) . |
| WO 93 25563 | 12/1993 | (WO) . |
| WO 95/08556 | 3/1995 | (WO) . |
| WO 97 31256 | 8/1997 | (WO) . |
| WO 97 49769 | 12/1997 | (WO) . |
| WO 99 34014 | 7/1999 | (WO) . |

OTHER PUBLICATIONS

Stratagene, Catalog, p. 39, 1988.*
Lee, R., Kaushik, N., Modak, M., Vinayak, R. and Pandey, V. "Polyamide nucleic acid targeted to the primer binding site of the HIV–1 RNA genome blocks in vitro HIV–1 reverse transcription" Biochemistry 37:900–10 (1998).
Lutz, M.J., Benner, S.A., Hein, S., Breipohl, G. & Uhlmann, E. "Recognition of uncharged polyamide–linked nucleic acid analogs by DNA Polymerases and reverse transcriptatses", J. Am. Chem. Soc. 119:3177–78 (1997).

(List continued on next page.)

Primary Examiner—Jezia Riley
(74) Attorney, Agent, or Firm—Alex Andrus

(57) ABSTRACT

The invention provides methods and a kit for primer extension of PNA-DNA chimera from template nucleic acids using polymerases, nucleotide 5'-triphosphates, and primer extension reagents. Structural requirements of the chimera for primer extension include 5 to 15 contiguous PNA monomer units, 3 or more contiguous nucleotides, and a 3' hydroxyl terminus. The chimera and/or a nucleotide is labelled with fluorescent dyes or other labels. The methods include DNA sequencing, DNA fragment analysis, reverse transcription, mini-sequencing, chromosome labelling, amplification, and single nucleotide polymorphism (SNP) detection.

43 Claims, 17 Drawing Sheets

OTHER PUBLICATIONS

Misra, H., Pandey, P., Modak, M. Vinayak, R. and Pandey, V. "Polyamide nucleic acid–DNA chimera lacking the phosphate backbone are novel primers for polymerase reaction catalyzed by DNA polymerases" Biochemistry 37:1917–25 (1998).

Ross, P., Lee, K. and Belgrader, P. "Discrimination of single–nucleotide polymorphisms in human DNA using peptide nucleic acid probes detected by MALDI–TOF mass spectrometry" Anal. Chem. 69:4197–4202 (1997).

Van der Laan, A., Brill, R., Kuimelis, R., Kuyl–Yeheskiely, E., van Boom, J., Andrus, A. and Vinayak, R. "A convenient automated solid–phase synthesis of PNA–(5')–DNA–(3')–PNA chimera", Tetrahedron Lett. 38:2249–52 (1997).

Vinayak, R., van der Laan, A., Brill, R., Otteson, K., Andrus, A., Kuyl–Yeheskiely, E. and van Boom, J. "Automated chemical synthesis of PNA–DNA chimera on a nucleic synthesizer", Nucleosides & Nucleotides 16:1653–56 (1997).

Uhlmann, E. "Peptide nucleic acids (PNA) and PNA–DNA chimera: from high binding affinity towards biological function" Biol Chem 379:1045–52 (1998).

Uhlmann, E., Will, D., Breipohl, G., Langner, D. and Ryte, A. "Synthesis and properties of PNA–DNA chimera" Angew. Chem., Intl. Ed. Eng. 35:2632–35 (1996).

* cited by examiner

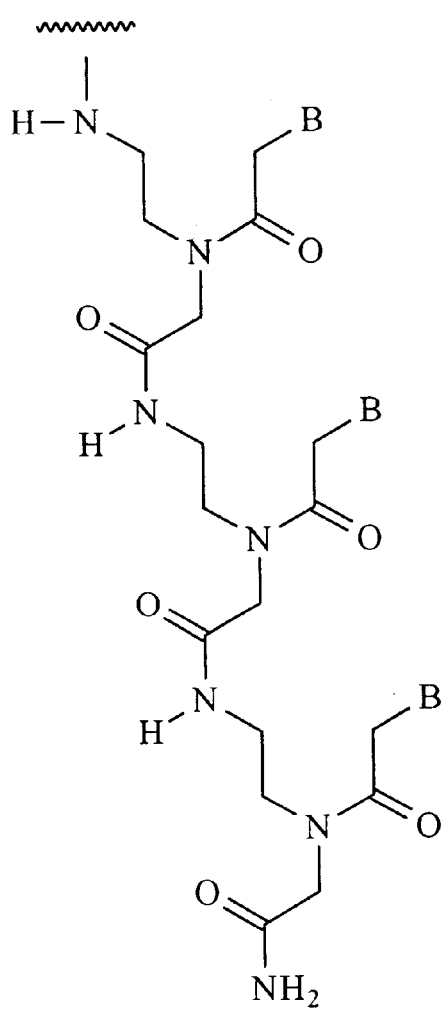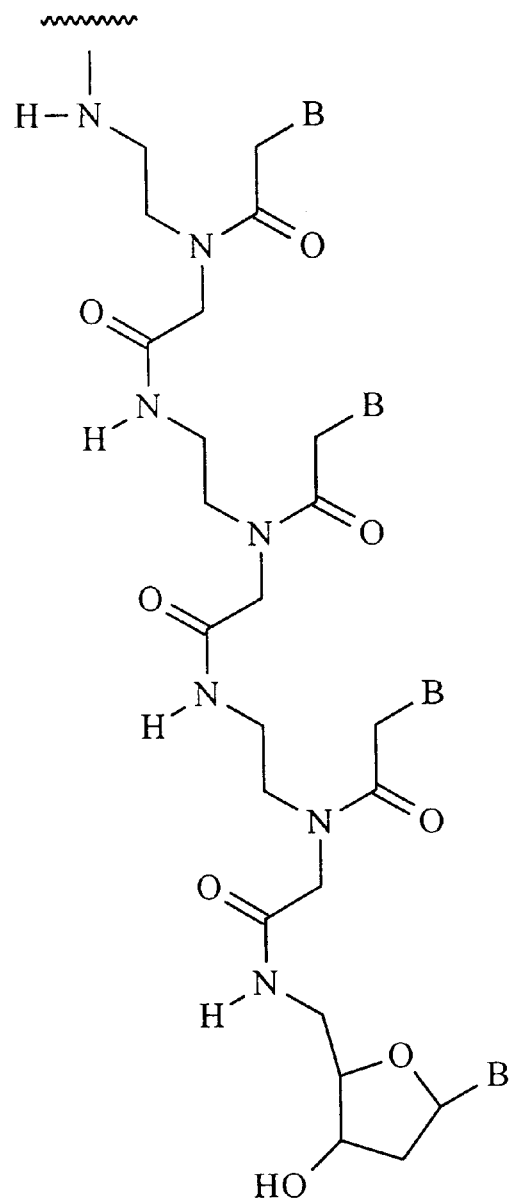
Figure 1AFigure 1B

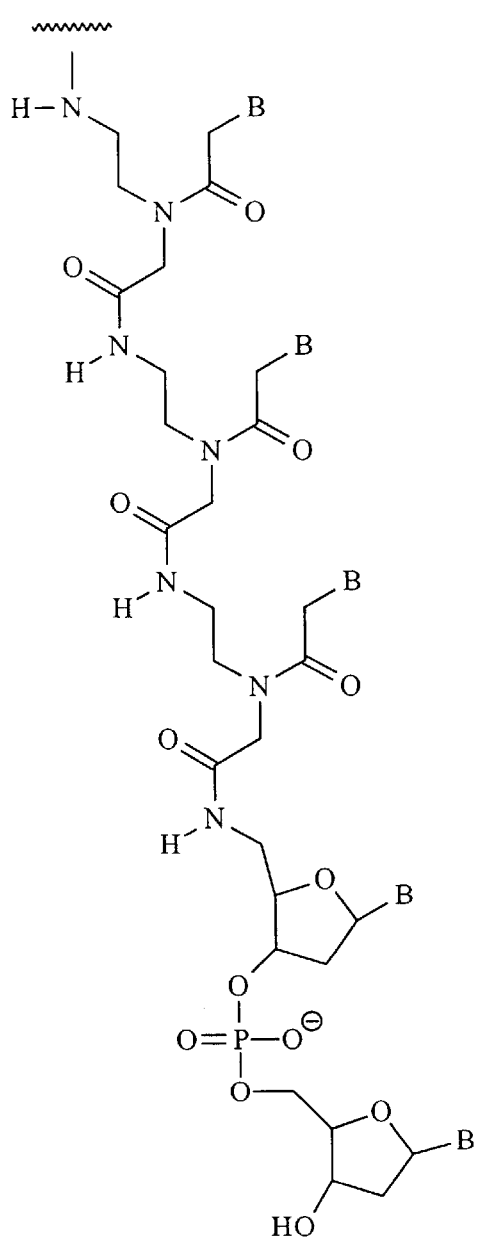
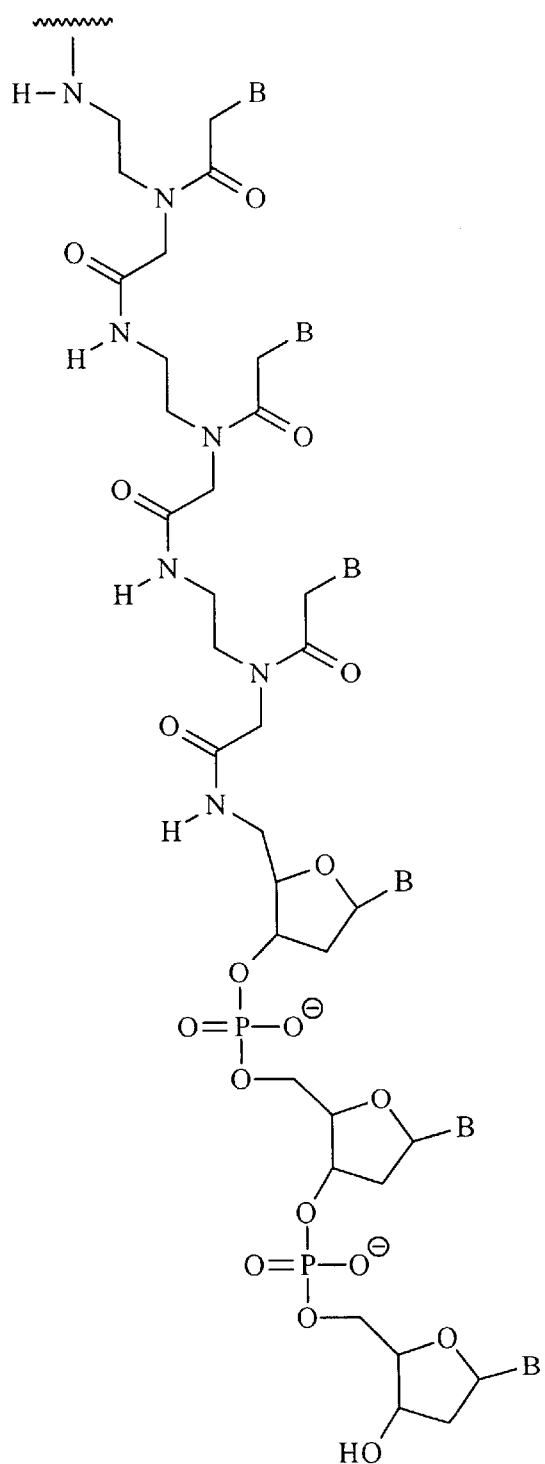
Figure 1C
Figure 1D

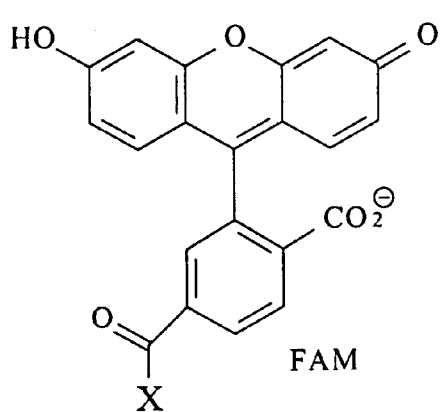
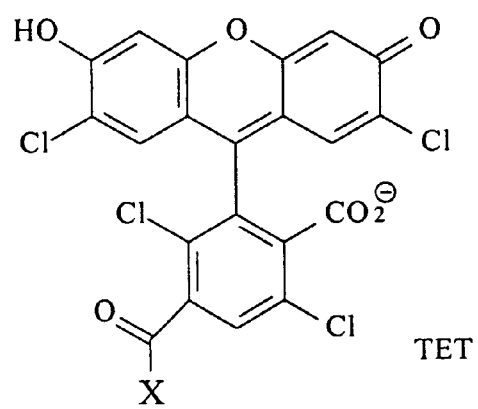
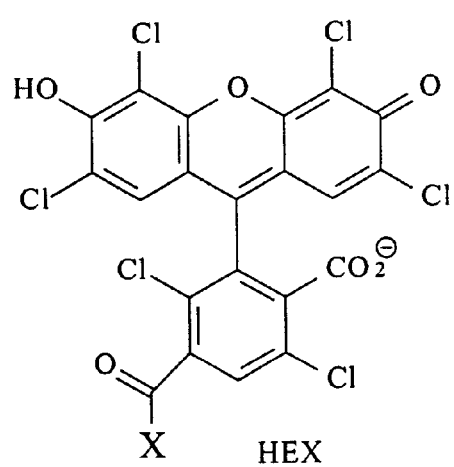
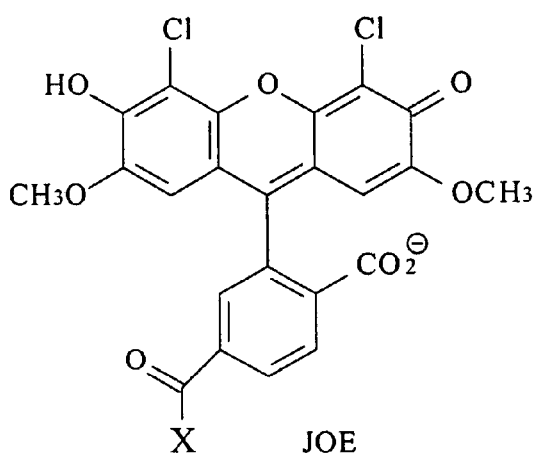
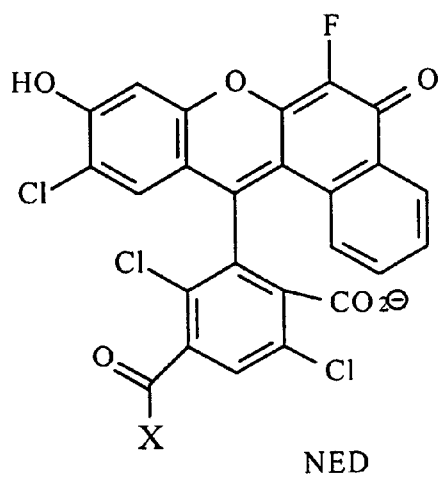
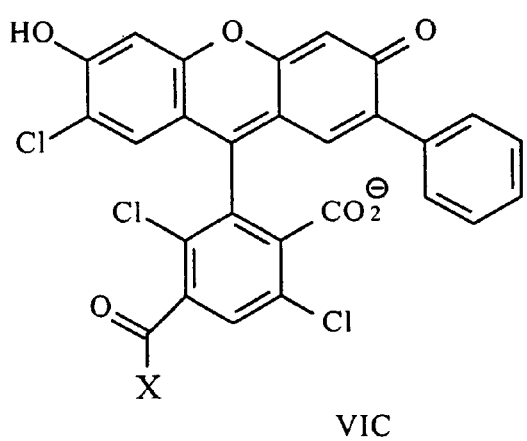
Figure 3A

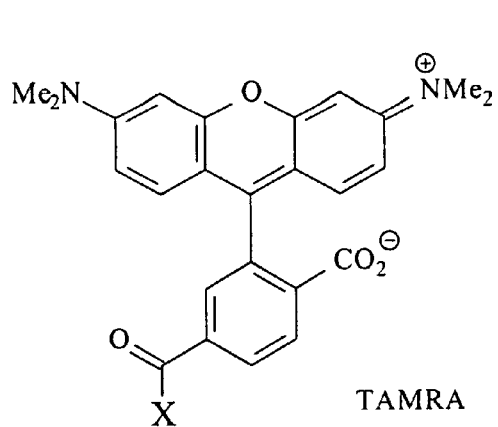
TAMRA
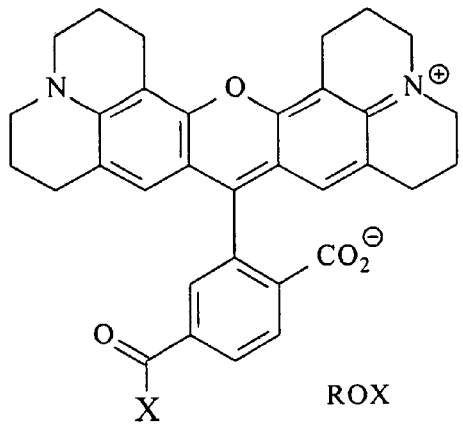
ROX
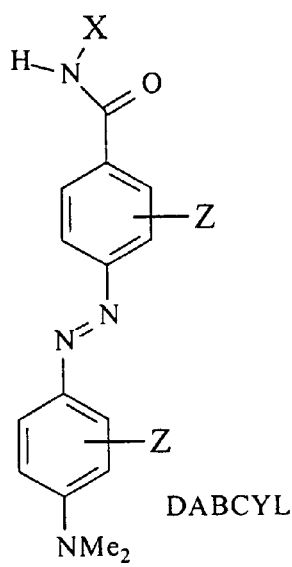
DABCYL
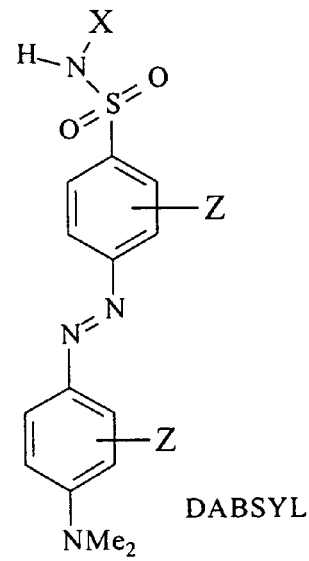
DABSYL
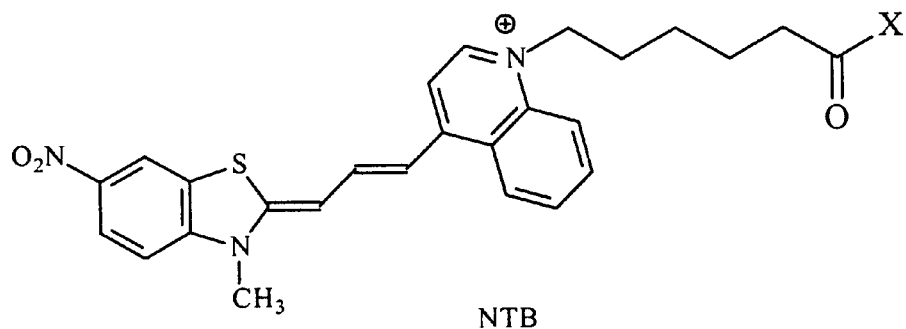
NTB
Figure 4

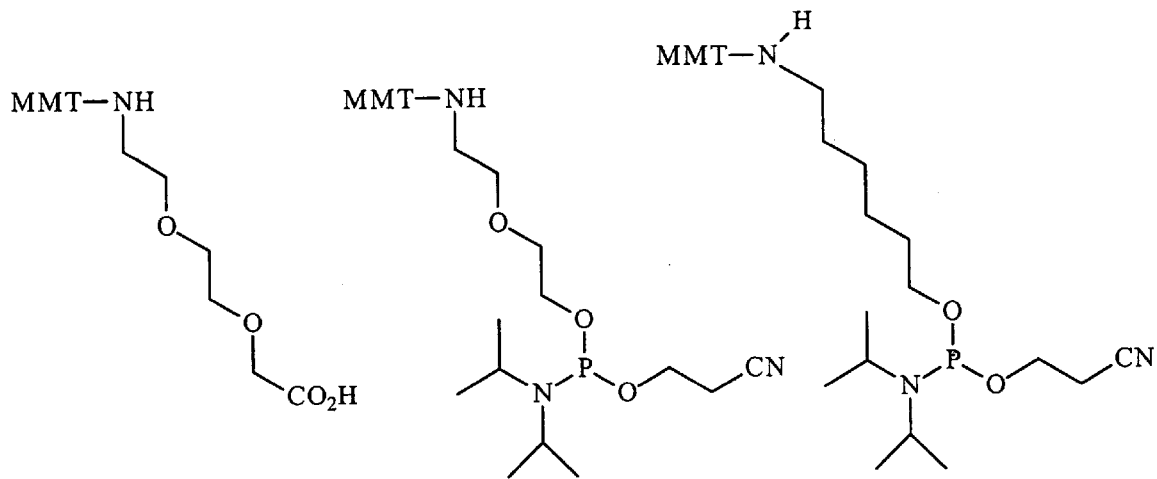
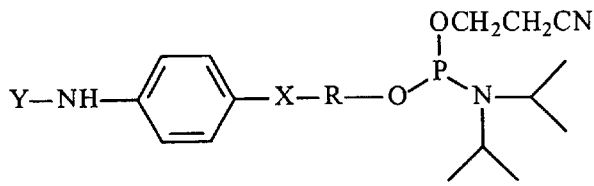
X = amide, urea, $CH_2$, O, or R
R = $(CH_2)_n$ or $(CH_2CH_2O)_n$
n = 1 - 10
Y = trifluoroacetyl, Fmoc, trityl, MMT, DMT
Figure 5

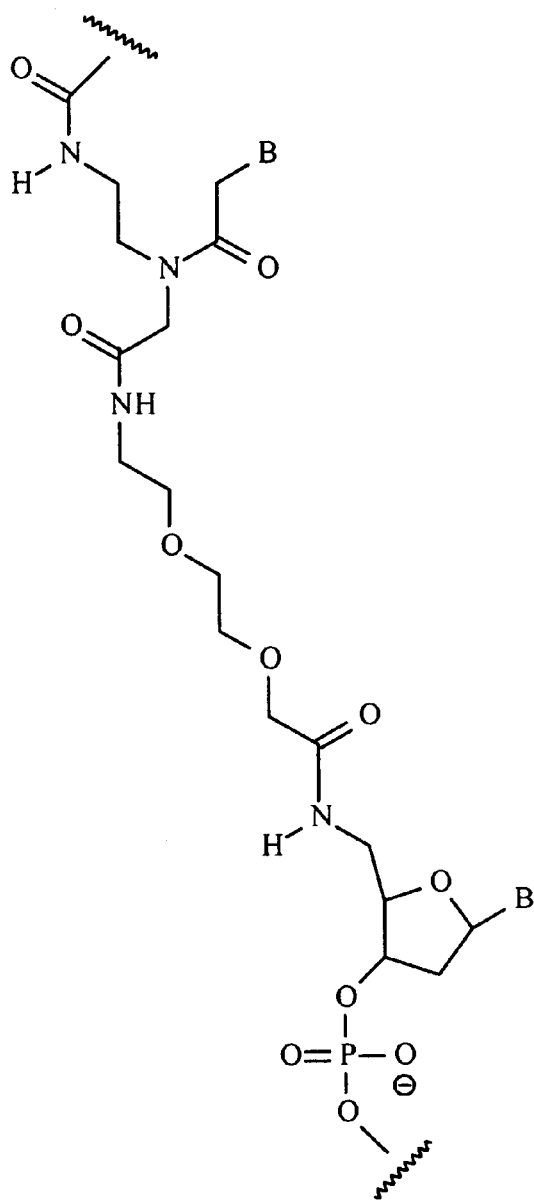
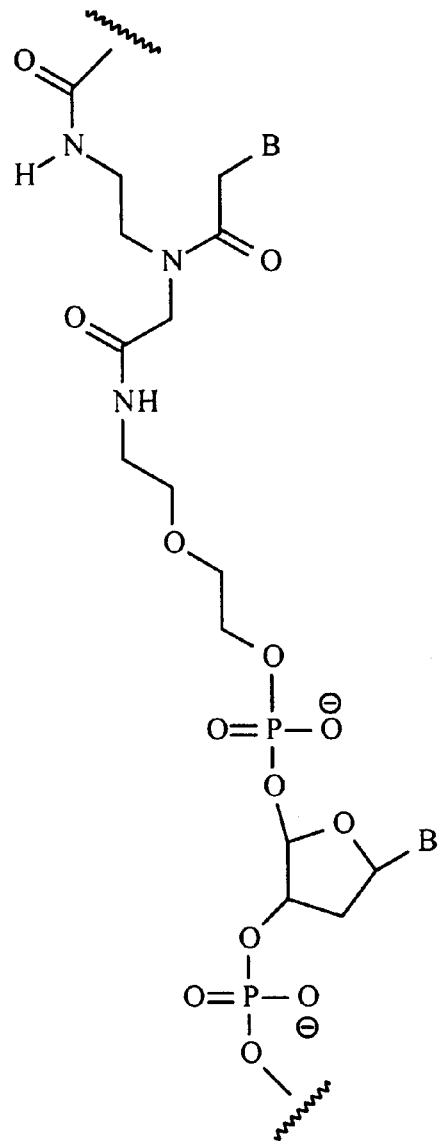
Figure 6A                     Figure 6B

15% Denaturing PAGE

POLYMERASE EXTENSION AT 3' TERMINUS OF PNA-DNA CHIMERA

FIELD OF THE INVENTION

The invention relates generally to the fields of enzymology and nucleic acid analogs. Specifically, this invention is directed to template-dependent, primer extension of PNA-DNA chimera using polymerase enzyme and nucleotide 5'-triphosphates.

BACKGROUND

One of the most powerful and versatile tools available to molecular biologists is the in vitro replication of nucleic acid sequences by primer extension, as exemplified by the ubiquitous techniques of polymerase chain reaction (PCR) (Mullis, 1987) and DNA sequencing (Sanger, 1977). Both techniques include the steps of: 1) hybridizing a short, e.g. 15–30 nt, synthetic oligonucleotide primer to a single-stranded template nucleic acid; and 2) enzymatically extending from the 3' hydroxyl terminus of the primer in the presence of nucleotide 5'-triphosphates, complementary to the template strand, and a polymerizing enzyme. By this general primer extension method, sequencing information is generated, template nucleic acids are amplified or copied, and other genetic analysis tests are conducted. Results are optimized through the choice and concentrations of primers, multiple primers, enzymes, nucleotides, and other reagents, and the selection of temperature, temperature cycling conditions, and other experimental conditions.

The choice of primers has been primarily limited to 2'-deoxyoligonucleotide primers made by the phosphoramidite chemistry method (Caruthers, 1983) on automated synthesizers (Caruthers, 1984). Whereas nucleic acid analogs are known which efficiently hybridize to DNA or RNA, some with comparable or superior hybridization specificity and/or affinity, enzyme-mediated formation of a new phosphodiester bond only occurs between a primer having a 3' terminal hydroxyl and a nucleotide having a 5'-triphosphate, or a closely related isostere, i.e. α-thiotriphosphate, etc. Most structural permutations in either the primer or the nucleotide severely compromise the efficiency of primer extension, or negate it totally.

Nucleic acid analogs are structural analogs of DNA and RNA and which are designed to hybridize to complementary nucleic acid sequences. Through modification of the internucleotide linkage, the sugar, and/or the nucleobase, nucleic acid analogs may attain any or all of the following desired properties: 1) optimized hybridization specificity or affinity, 2) nuclease resistance, 3) chemical stability, 4) solubility, 5) membrane-permeability, and 6) ease or low costs of synthesis and purification.

A useful and accessible class of nucleic acid analogs is the family of peptide nucleic acids (PNA) in which the sugar/phosphate backbone of DNA or RNA has been replaced with acyclic, achiral, and neutral polyamide linkages. The 2-aminoethylglycine polyamide linkage in particular has been well-studied and shown to impart exceptional hybridization specificity and affinity when nucleobases are attached to the linkage through an amide bond (Buchardt, 1992; Nielsen, 1991).

2-Aminoethylglycine PNA oligomers (FIG. 1A) typically have greater affinity, i.e. hybridization strength and duplex stability for their complementary PNA, DNA and RNA, as exemplified by higher thermal melting values (Tm), than the corresponding DNA sequences. The melting temperatures of PNA/DNA and PNA/RNA hybrids are much higher than corresponding DNA/DNA or DNA/RNA duplexes (generally 1° C. per bp) due to a lack of electrostatic repulsion in the PNA-containing duplexes. Also, unlike DNA/DNA duplexes, the Tm of PNA/DNA duplexes are largely independent of salt concentration. The 2-aminoethylglycine PNA oligomers also demonstrate a high degree of base-discrimination (specificity) in pairing with their complementary strand. Specificity of hybridization can be measured by comparing Tm values of duplexes having perfect Watson/Crick complementarity and those with one or more mismatches. The degree of destabilization of mismatches, measured by the decrease in Tm (ΔTm), is a measure of specificity. In addition to mismatches, specificity and affinity are affected by structural modifications, hybridization conditions, and other experimental parameters. The neutral backbone of PNA also increases the rate of hybridization significantly in assays where either the target, template, or the PNA probe is immobilized on a solid substrate. Without any electrostatic repulsion, the rate of hybridization is often much higher for PNA probes than for DNA or RNA probes in applications such as Southern blotting, northern blots, or in situ hybridization experiments (Corey, 1995). Unlike DNA, PNA can displace one strand, "strand invasion", of a DNA/DNA duplex (Kuhn, 1999). With certain DNA sequences, a second PNA can further bind to form an unusually stable triple helix structure $(PNA)_2/DNA$. PNA have been investigated as potential antisense agents, based on their sequence-specific inhibition of transcription and translation (Von Matt, 1999; Lee, 1998; Nielsen, 1996). PNA oligomers themselves are not substrates for polymerase as primers or templates, and do not conduct primer extension with nucleotides (Demers, 1997, see col. 2, lines 55–56).

PNA-DNA chimera are oligomer molecules with discrete PNA and nucleotide moieties. They can be synthesized by covalently linking PNA monomers and nucleotides in virtually any combination or sequence. Efficient and automated methods have been developed for synthesizing PNA-DNA chimera (Vinayak, 1997; Uhlmann, 1996; Van der Laan, 1997). PNA-DNA chimera are designed to have desirable properties found in PNA and DNA, e.g. superior hybridization properties of PNA and biological functions like DNA (Uhlmann, 1998).

Attempts to demonstrate primer extension of PNA-DNA chimeric primers with radioisotopically-labelled nucleotides have been reported. Primer extension on an 8 Int DNA template was attempted from a complementary PNA-DNA chimera with 15 PNA monomer units linked through an amide bond to a single 3' terminal thymidine nucleoside (FIG. 1B), various polymerases, and nucleotides dATP, dGTP, dTTP, and $^{32}$P-dCTP (Lutz, 1998). Some incorporation of nucleotides and extension may be evident, but due to the unavailability of proper control experiments, the level of incorporation is unknown.

Primer extension was also reported using a mixture of PNA-DNA chimera consisting of 19 PNA monomer units with three (FIG. 1D) and four 2'-deoxynucleotides, labelled once and twice respectively, with $^{32}$P dCTP and terminal transferase (Misra, 1998). The 3' hydroxyl terminus was extended on a 49 nt DNA template and a 30 nt RNA template with unlabelled nucleotide 5'-triphosphates. Autoradiography of the gel after electrophoresis showed a ladder of radiolabelled products, the majority of which was unextended chimera, indicating inefficient primer extension. This experiment employed a relatively long PNA moiety, 19 monomer units, incurring the attendant costs, loss of specificity, and synthesis inefficiencies of a longer chimera oligomer.

In another study, chimera consisting of 3 PNA monomer units and either 2,4,6,9, or 12 deoxynucleotides were extended with Klenow polymerase from an 18 nt DNA template (Reeve, 1995). All chimera had T deoxynucleotide at the linkage between the PNA and DNA moieties. Detection of incorporated $^{32}$P-dCTP by autoradiography indicated that all the chimera except the one with 2 deoxynucleotides were extended. However, no quantitative or qualitative data was provided. Given the sensitivity of autoradiography, extension of the chimera in this study may have been at a detectable, but not useful, level.

Fluorescence has largely supplanted radioactivity as the preferred detection method for most primer extension applications, such as automated DNA sequencing, in vitro DNA probe-based diagnostics, nucleic acid amplification, DNA fragment analysis, and transcriptional expression mapping and profiling. It is thus desirable to provide methods by which PNA-DNA chimera can be enzymatically extended to form non-radioisotopically labelled extension products. DNA sequencing methods benefit from the use of PNA-DNA chimera as primers, in particular where the template is double-stranded or where random priming is conducted with an array of a large number of chimera, or mixed-base sequence chimera. The increased affinity and specificity conferred by the PNA moiety in a PNA-DNA chimera allows for shorter primers. Shorter primers are more economical and require less sequence information. Such methods would improve assays and tests based on primer extension, e.g. greater precision and accuracy.

SUMMARY

The invention relates to chimera molecules of PNA and DNA monomer units and their use in primer-extension methods, such as DNA sequencing and nucleic acid amplification, to generate non-radioisotopically labelled extension products.

The invention provides methods for enzymatic extension of PNA-DNA chimera primers to generate labelled primer extension products. The invention is based on the discovery that a PNA-DNA chimera can conduct primer extension under a broad range of experimental conditions and variables. PNA-DNA chimeras of the invention include two moieties covalently linked together: i) a contiguous moiety of 5 to 15 PNA monomer units, and ii) a contiguous moiety of at least three nucleotides. The nucleotide moiety has an enzymatically-extendable terminus, such that the PNA-DNA chimera can be enzymatically extended.

In a first aspect, the invention provides a method of producing a template-dependent, non-radioisotopically labelled chimeric extension product by enzymatically extending a PNA-DNA chimera primer annealed to a template nucleic acid in the presence of a polymerase and a primer extension reagent (FIG. 2). The primer extension reagent comprises a nucleotide 5'-triphosphate capable of supporting template-dependent extension. The chimera and/or the nucleotide 5'-triphosphate may be labelled with a non-radioisotopic label such that the extension products are non-radioisotopically labelled. In one illustrative embodiment of the invention, the PNA-DNA chimera has the formula: $P_x$—L—$N_y$ 3', where each P is independently a PNA monomer, x is an integer from 5 to 15, L represents a covalent linkage between P and N, each N is independently a nucleotide, y is an integer from 3 to 15, and the 3' terminal N has a 3' hydroxyl group (FIG. 1D).

In one embodiment of the method, the extension reagent comprises a mixture of nucleotide 5'-triphosphates capable of incorporation and creation of an extended primer with a 3' hydroxyl, and capable of further, continuous extension, e.g. 2'-deoxyribonucleotides (dNTP) and ribonucleotides (NTP). The reagent may further include one or more terminator nucleotides capable of incorporation, e.g. 2',3'-dideoxynucleotides (ddNTP) and 2,3'-dideoxy-dehydronucleotides, that, once incorporated, terminate further extension. In another embodiment, the reagent comprises only terminator nucleotides and does not include nucleotide 5'-triphosphates capable of continuous extension.

In a preferred embodiment, the PNA moiety, i.e., $P_x$, of the PNA-DNA chimera is a 2-aminoethylglycine peptide nucleic acid.

The DNA moiety, i.e., $N_y$, of the PNA-DNA chimera may be comprised of 2'-deoxynucleotides (DNA), ribonucleotides (RNA), and modified sugars or internucleotide linkages thereof, especially those that confer greater specificity, affinity, rates of hybridization, and chemical stability.

In embodiments employing a labelled PNA-DNA chimera, the PNA-DNA chimera may be labelled at: (i) a nucleobase, e.g. the N-9 or C-8 positions of a purine or a deazapurine nucleobase, or the C-5 position of a pyrimidine nucleobase; (ii) a sugar; (iii) the aminoethylglycine backbone; or (iv) an amino, a sulfide, a hydroxyl, and/or a carboxyl group. Preferably, the chimera is labelled at the amino terminus of the PNA moiety. In embodiments employing a labelled nucleotide, the nucleotide 5'-triphosphate is preferably labelled at the nucleobase, but may also be labelled at other positions provided that the label does not interfere with enzymatic incorporation. Labels may be fluorescent dyes (FIGS. 3A–3B), fluorescence quenchers (FIG. 4), hybridization-stabilizers, energy-transfer dye pairs, electrophoretic mobility modifiers, chemiluminescent dyes, amino acids, proteins, peptides, enzymes, and affinity ligands. Preferably, the label is detectable upon illumination with light, e.g. laser sources at infrared, visible or ultraviolet excitation wavelengths.

The linkage, L, between the PNA and DNA moieties is preferably a bond, e.g. the carbonyl-nitrogen bond in an amide group where the moieties are linked without intervening atoms (FIGS. 1B–1D). In another embodiment, the linkage may be a multi-atom linker, e.g. an alkyldiyl consisting of 1 to 20 carbon atoms, an alkyldiyl consisting of 6 to 20 carbon atoms, optionally including one or more heteroatoms, O linker, or 1 to 6 ethyleneoxy units, —($CH_2CH_2O$)— (FIGS. 6A–6B).

The template or target nucleic acid can be any nucleic acid or nucleic acid analog capable of mediating template-directed nucleic acid synthesis. Examples of suitable template nucleic acids include, e.g., genomic DNA, DNA digests, plasmids, vectors, viral DNA, PCR products, RNA, and synthetic nucleic acids. The template nucleic acid may also be a metaphase or interphase chromosome. Preferably, the chromosome is denatured prior to PNA-DNA chimera hybridization and primer extension. Template nucleic acids may be single-stranded or double-stranded. Templates are typically larger than the PNA-DNA chimera primer and can range from as few as about 20–30 to as many as millions of nucleotides (nt) or base-pairs (bp), depending on the particular application.

Suitable enzymes to extend the PNA-DNA chimera primers depend on the composition of the template nucleic acid. Reverse transcriptases may be used for extending RNA templates, e.g. mRNA. DNA polymerase may be used for extending DNA templates.

The template nucleic acid or the PNA-DNA chimera may be immobilized on a solid substrate. When immobilized, the template or chimera is preferably covalently attached to the solid substrate, e.g. via a terminal monomer unit.

In a second aspect of the invention, a kit for primer extension is provided which comprises: (i) a PNA-DNA chimera having from 5 to 15 contiguous PNA monomer units, from 3 to 15 contiguous nucleotides, and a 3' hydroxyl terminus; (ii) one or more enzymatically extendable nucleotide 5'-triphosphates and; (iii) a polymerase enzyme. The chimera and/or a nucleotide 5'-triphosphate is labelled with a non-radioisotopic label. In another embodiment, the kit additionally includes a template comprising a sequence complementary to the chimera or containing one or more mismatches to the chimera.

In a third aspect, the invention provides methods for sequencing a template nucleic acid by enzymatically extending a PNA-DNA chimera primer hybridized to the template in the presence of a polymerase and a terminating nucleotide 5'-triphosphate. The chimera or the nucleotide 5'-triphosphate is non-radioisotopically labelled. Generally, the methods for sequencing a template nucleic acid comprise the steps of: (i) generating a series of differently-sized primer extension products by enzymatically extending a PNA-DNA chimera annealed to the template nucleic acid in the presence of a polymerase, a mixture of nucleotide 5'-triphosphates capable of supporting continuous primer extension and at least one terminating nucleotide 5'-triphosphate; (ii) separating the primer extension product from one another, typically based on size; and (iii) determining the sequence of the template nucleic acid.

In one embodiment, a nested set of labelled primer extension products, i.e. a set in which each extension product is one nt shorter than the preceding extension product of the set, are generated by a mixture of enzymatically-extendable nucleotide 5'-triphosphates capable of supporting continuous primer extension. Where either the PNA-DNA chimera or the terminating nucleotide 5'-triphosphate bears a non-radioisotopic label, the identity of certain bases is revealed by the labels, as is well known in the art of nucleic acid sequencing (Bergot, 1994; Lee, 1992, Smith, 1998). In one convenient embodiment, a mixture of four different labelled terminating nucleotides is used, e.g. ddATP, ddCTP, ddGTP, ddTTP, each bearing a different, determinable label, such that the 3'-terminus nucleotide of each primer extension product is revealed by the identity of the label. Alternatively, the method can be performed in the absence of nucleotide 5'-triphosphates capable of supporting continuous primer extension such that only a single terminating nucleotide is added (Goelet, 1999; Syvanen, 1990).

The methods of the present invention are well-suited to fluorescent detection, particularly the simultaneous detection of multiple spectrally-resolvable fluorescent dyes. The methods are particularly well-suited for detecting, identifying, or determining classes of primer extension products that have been subjected to a separation procedure, such as electrophoresis, or that have been distributed amongst locations in a spatially-addressable hybridization array.

In a fourth aspect, a method is provided for reverse transcription of RNA by enzymatically extending a primer-template RNA hybrid in the presence of a reverse transcriptase and a mixture of enzymatically-extendable nucleotide 5'-triphosphates capable of supporting continuous primer extension. The primer is a PNA-DNA chimera and either said primer or a nucleotide 5'-triphosphate is non-radioisotopically labelled.

In a fifth aspect, a method is provided for in situ chromosome targetting by single or multiple labelling where the chromosome is denatured and either in metaphase or interphase. A primer-chromosome hybrid is enzymatically extended in the presence of a DNA polymerase and a mixture of nucleotide 5'-triphosphates capable of supporting continuous primer extension. The primer is a PNA-DNA chimera. Either the primer or a nucleotide 5'-triphosphate is non-radioisotopically labelled. Fluorescence at the chimera binding sites on the chromosome can be detected.

In a sixth aspect, a method is provided for DNA amplification where amplification products are generated by enzymatically extending a primer-template nucleic acid in the presence of two primers, a DNA polymerase and a mixture of enzymatically-extendable nucleotide 5'-triphosphates capable of supporting continuous primer extension. One or both of the primers is a PNA-DNA chimera. Either the primers or nucleotide 5'-triphosphates are non-radioisotopically labelled. The temperature is cycled to effect denaturation, annealing, and primer extension to form an amplification product by extension of the primers with the nucleotide 5'-triphosphates. One or both of the 5' terminii of the amplification product bears the PNA sequence of the chimera primers.

In one embodiment, the amplification product is immobilized by hybridization on a solid substrate comprising a nucleic acid having a sequence complementary to the PNA moiety of the amplification product.

These and other aspects, objects, features, and advantages of the present invention will become better understood with reference to the following description, drawings, examples, and appended claims.

BRIEF DESCRIPTION OF THE DRAWINGS

FIGS. 1A–1D Structures of N-(2-aminoethyl)-glycine PNA (1A) and PNA-DNA chimera with one (1B), two (1C), and three (1D) 2'-deoxynucleotides, where B is a nucleobase. The wavy line segment represents continuing, repeating units.

FIGS. 3A–3B Fluorescent dye label structures: FAM, TET, HEX, JOE, NED, VIC (3A); dJON, dR139, JODA, FAM donor (3B). X denotes an attachment site.

FIG. 4 Quencher label structures: TAMRA, ROX, DABCYL, DABSYL, NTB. X denotes an attachment site. X denotes an attachment site. Z is H or $NO_2$.

FIG. 5 Linker reagents for linkers between PNA and DNA moieties in chimera.

FIGS. 6A–6B PNA-DNA chimera with bis-ethyleneoxy-acetamido linker (6A) and bis-ethyleneoxy-phosphate linker (6B).

| Lane | Primer | (SEQ. ID NO.) |
|---|---|---|
| 1 | none | |
| 2 | TAG TTC | 1 |
| 3 | TAG TTC - t | 2 |
| 4 | TAG TTC - ta | 3 |

-continued

| Lane | Primer | (SEQ. ID NO.) |
|---|---|---|
| 5 | TAG TTC - tag | 4 |
| 6 | TAG TTC - taga | 5 |
| 7 | 5' tag ttc 3' | 6 |
| 8 | 5' tag ttc tag 3' | 7 |
| M | DNA oligo ladder | |

PNA - UPPER CASE; DNA- lower case

Figure 8:
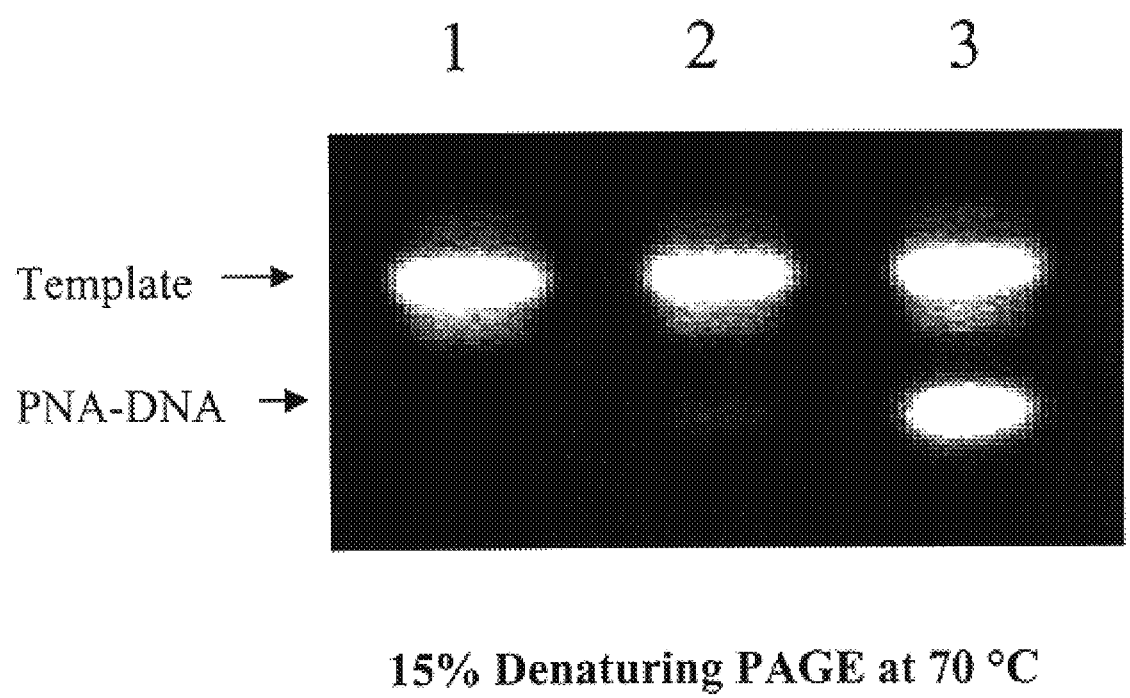

FIG. 8 Polyacrylamide (15%) gel electrophoresis under denaturing conditions (7M urea) and SYBR-Green staining. Primer extension of DNA 38 nt template (SEQ. ID NO. 8) with PNA-DNA chimera with Klenow (exo-) polymerase

| Lane | Primer | (SEQ. ID NO.) |
|---|---|---|
| 1 | Ac-TAG TTC T - ag | 9 |
| 2 | Ac-TAG TTC T - aga | 10 |
| 3 | Ac-TAG TTC T - agac | 11 |

Figure 9:
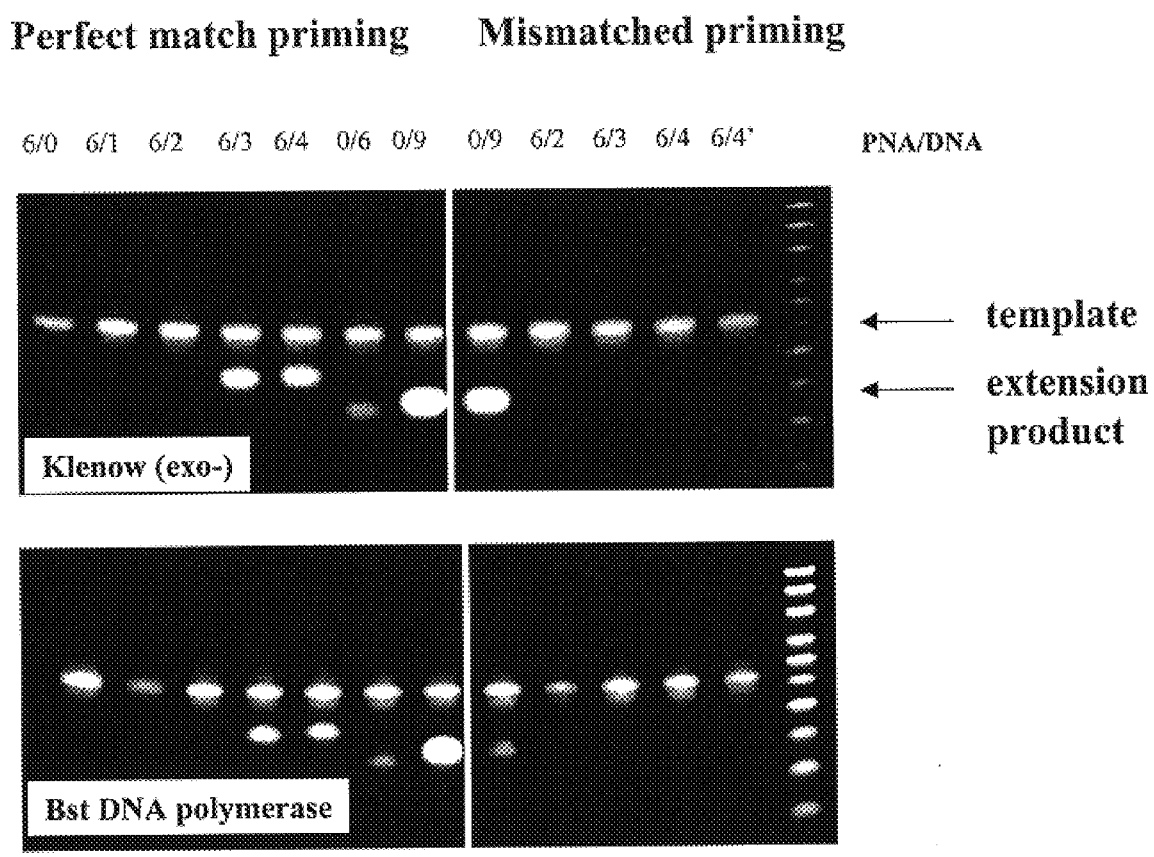

FIG. 9 Polyacrylamide (15%) gel electrophoresis under denaturing conditions (7M urea) and SYBR-Green staining. Specificity of DNA and PNA-DNA chimera primers with Klenow (top gel) and Bst polymerase (bottom gel), and perfect match 38 nt template (SEQ. ID NO. 8) (left side) and two mismatched templates (SEQ. ID NO. 12 and 13) (right side).

| Lane | Primer | (SEQ. ID NO.) |
|---|---|---|
| 6/0 | TAG TTC | 1 |
| 6/1 | TAG TTC - t | 2 |
| 6/2 | TAG TTC - ta | 3 |
| 6/3 | TAG TTC - tag | 4 |
| 6/4 (6/4') | TAG TTC - taga | 5 |
| 0/6 | 5' tag ttc 3' | 6 |
| 0/9 | 5' tag ttc tag 3' | 7 |
| | DNA oligo ladder | |

Figure 10:
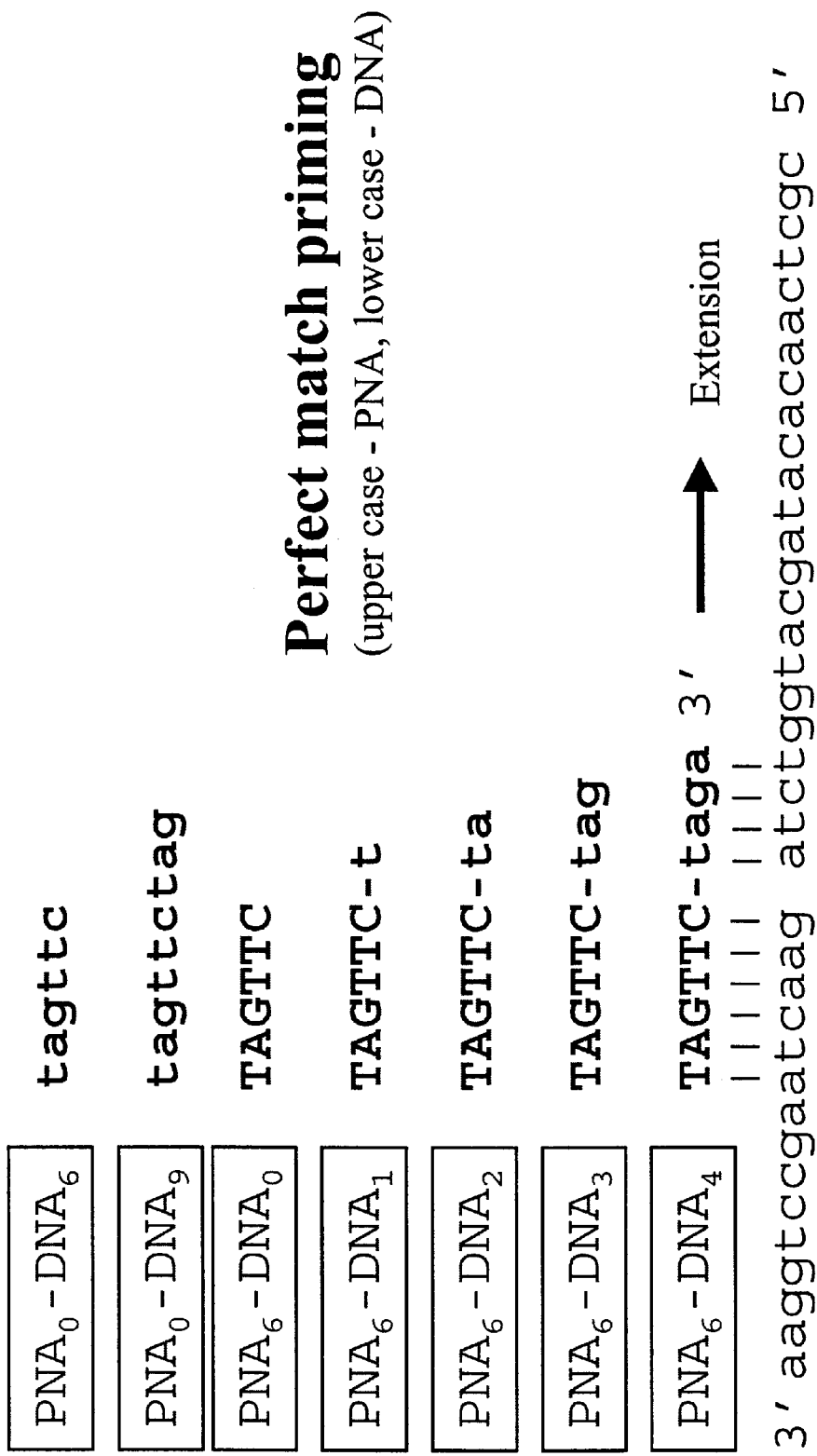

FIG. 10 Primer sequences on left side panels of FIG. 9 in perfect match priming of 38 nt DNA template (SEQ. ID NO. 8). (upper case—PNA, lower case—DNA)

Figure 11:
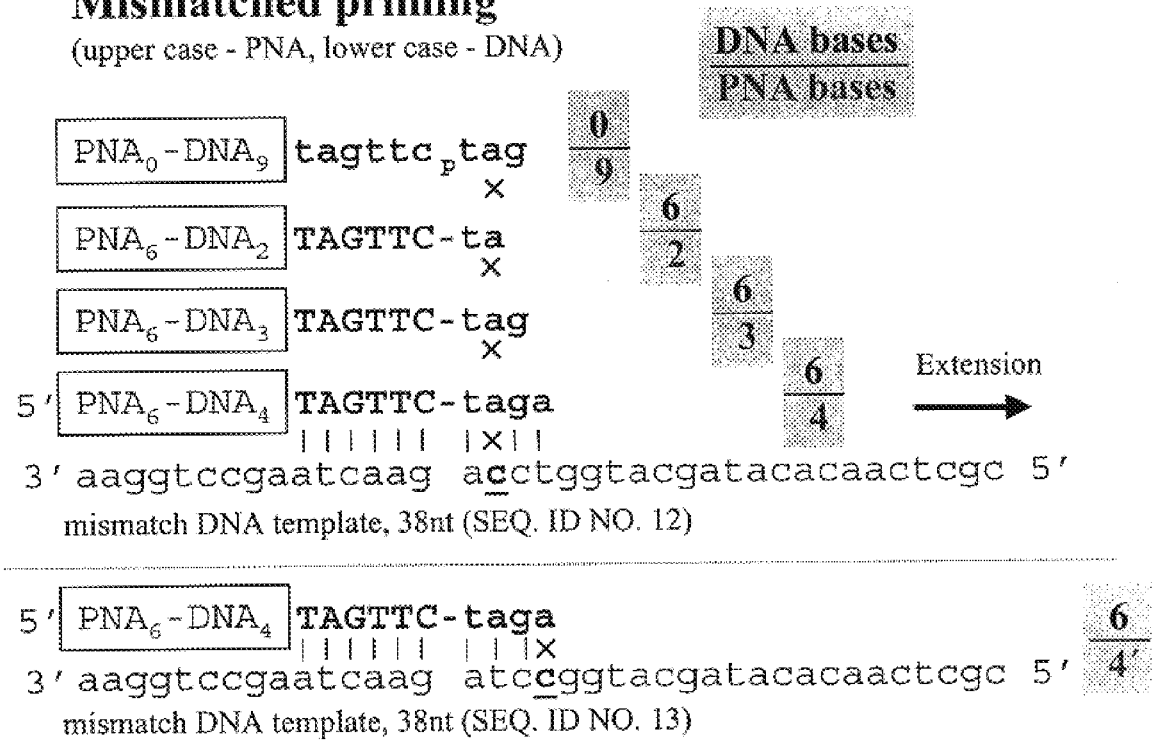

FIG. 11 Primer sequences on right side panels of FIG. 9 in mismatched priming of:

38 nt DNA template (SEQ. ID NO. 12) with one-base mismatch at the 2nd base (c), complementary to the 2nd base after the PNA-DNA linkage; and 38 nt DNA template (SEQ. ID NO. 13) with one-base mismatch at the 4th base (c), complementary to the 4th base after the PNA-DNA linkage in chimera primer 6/4'. (upper case—PNA, lower case—DNA)

Figure 7:
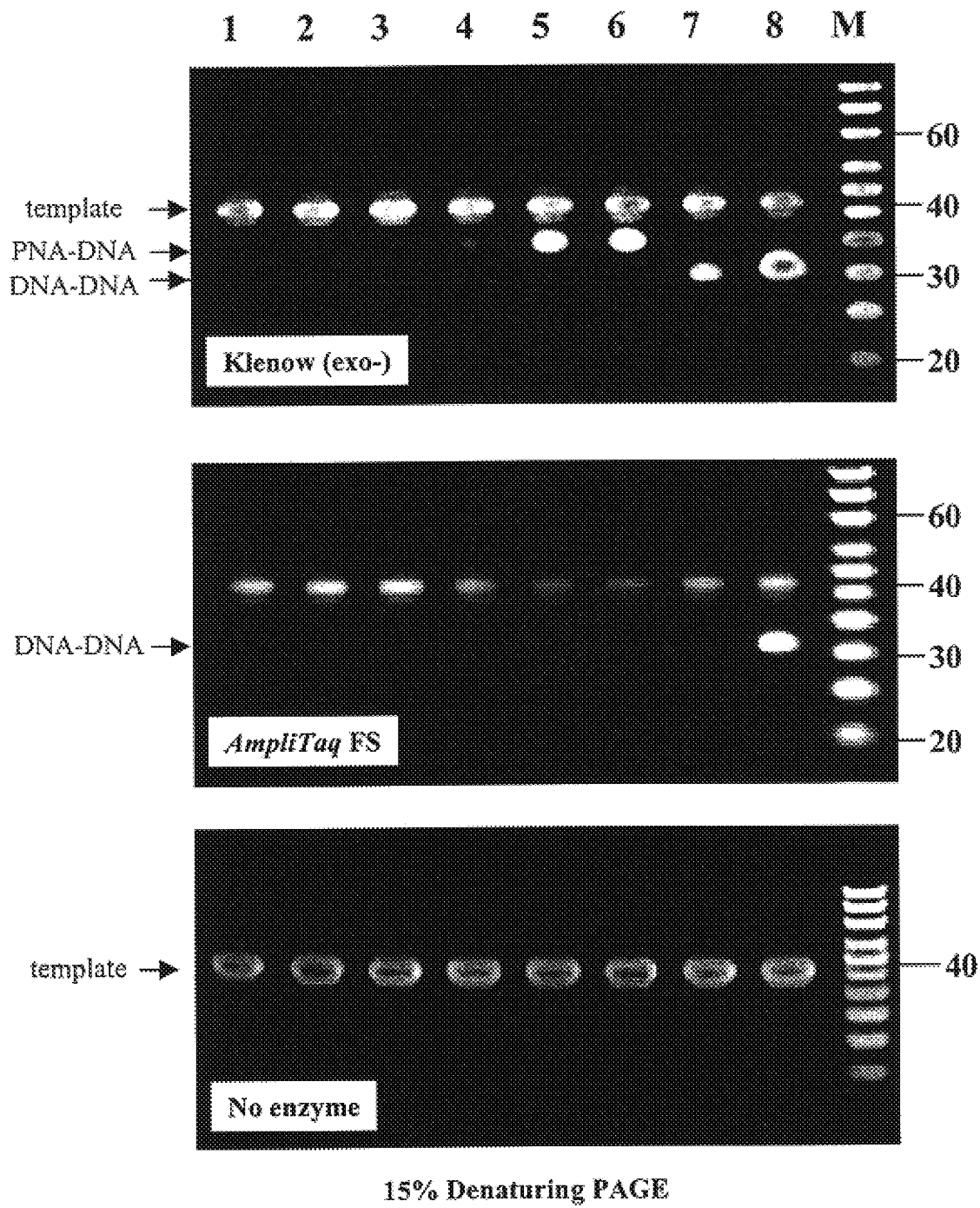
FIG. 7 Polyacrylamide (15%) gel electrophoresis under denaturing conditions (7M urea) and SYBR-Green staining. Primer extension of a DNA 38 nt template (SEQ. ID NO. 8) with various primers. Top panel: Klenow (exo-) polymerase, middle panel: AmpliTaq FS polymerase, bottom panel: no enznme
Figure 12:
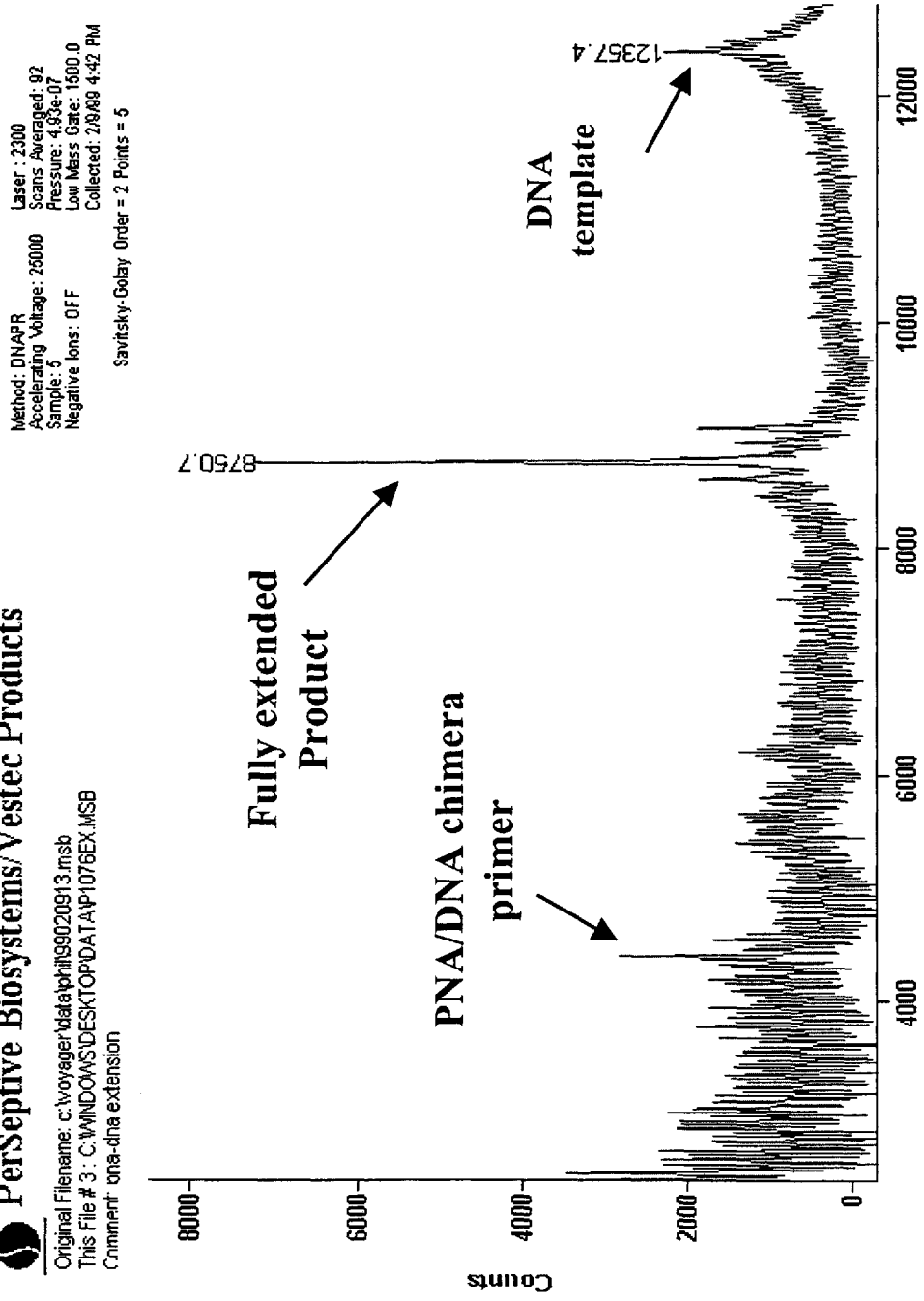

FIG. 12 MALDI-TOF mass spectroscopy of primer extension product, sample from lane 6, FIG. 7. MW 8750.7 of fully extended $PNA_6DNA_{23}$ product.

Figure 13:
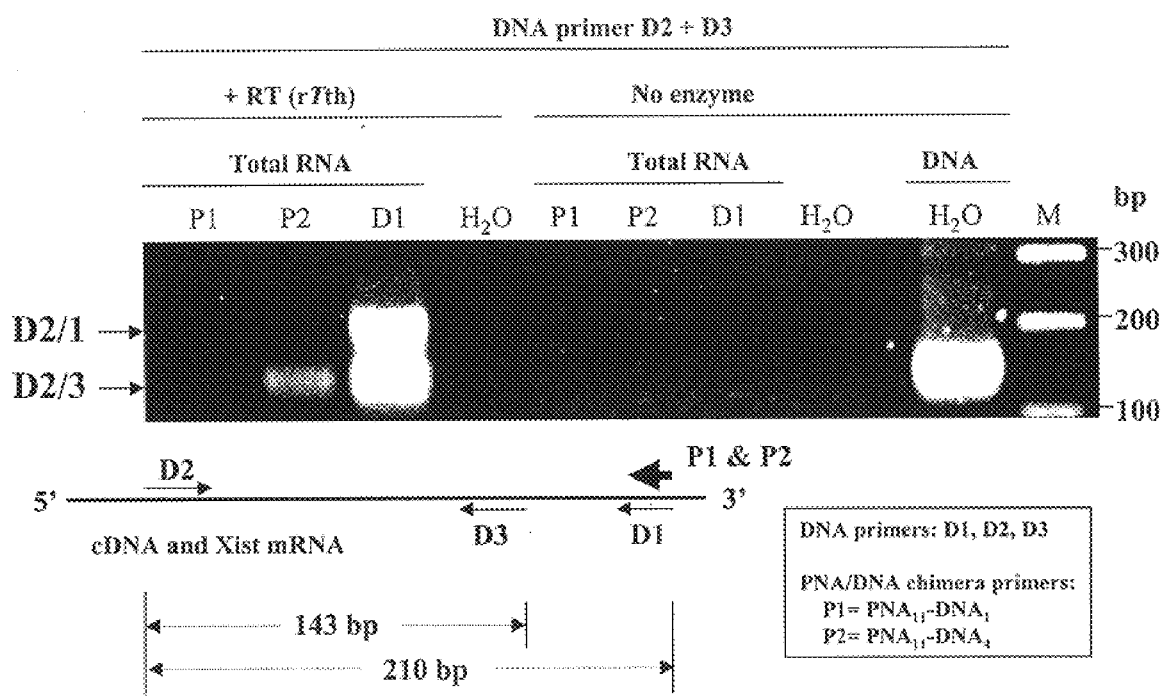

FIG. 13 Polyacrylamide gel electrophoresis under denaturing conditions (7M urea) and SYBR-Green staining. Mouse Xist gene mRNA was reverse transcribed with PNA-DNA chimera primer. The cDNA copy was amplified with D2 and D3 primers to give 143 bp and 210 bp fragments.

Figure 14:
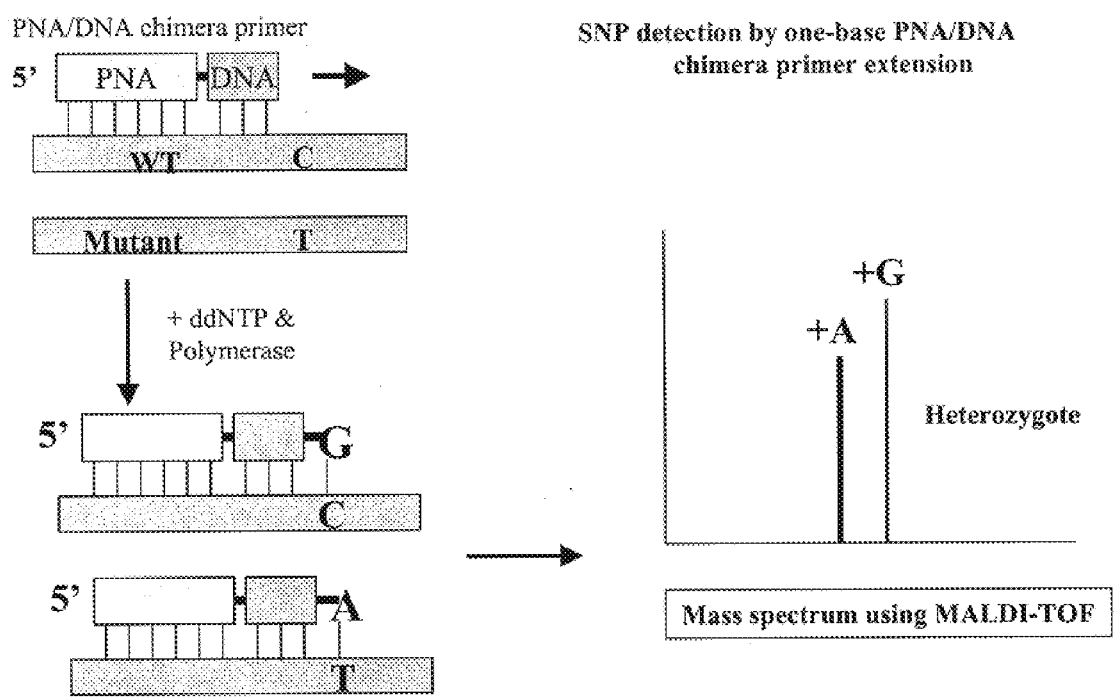

FIG. 14 Schematic of single nucleotide polymorphism (SNP) detection by one-base PNA-DNA chimera primer extension from wild type (WT) and mutant templates, and MALDI-TOF mass spectral analysis of extension products.

Figure 15:
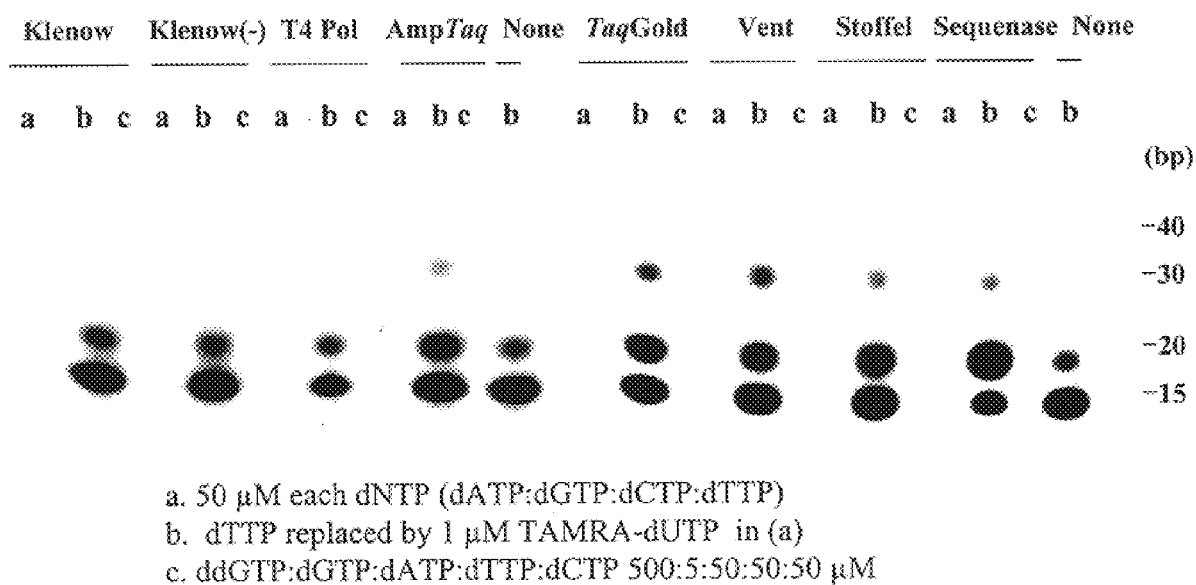

FIG. 15 Polyacrylamide (15%) gel electrophoresis under denaturing conditions with fluorescence detection (no staining). Detection of fluorescent labelled primer extension products by incorporation of TAMRA-dUTP with PNA-DNA chimera primer (SEQ. ID NO. 4) and 5' biotin DNA 38 nt template (SEQ. ID NO. 8).

DETAILED DESCRIPTION OF THE PREFERRED EMBODIMENTS

Reference will now be made in detail to the preferred embodiments of the invention. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises primer extension methods where the primer is a PNA-DNA chimera. The methods of the present invention find particular application in the area of nucleic acid analysis, e.g. DNA sequencing, fragment analysis, and detection of probe hybridization in hybridization assays.

DEFINITIONS

Unless stated otherwise, the following terms and phrases as used herein are intended to have the following meanings:

"Nucleobase" refers to a nitrogen-containing heterocyclic moiety, e.g. a purine, a 7-deazapurine, or a pyrimidine. Typical nucleobases are adenine, guanine, cytosine, uracil, thymine, 7-deazaadenine, 7-deazaguanine, and the like.

"Nucleoside" refers to a compound consisting of a nucleobase linked to the C-1'carbon of a ribose sugar.

"Nucleotide" refers to a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group includes sulfur substitutions for the various oxygens, e.g. α-thio-nucleotide 5'-triphosphates.

As used herein, the term "nucleic acid" encompasses the terms "oligonucleotide" and "polynucleotide" and means single-stranded and double-stranded polymers of nucleotide monomers, including 2'-deoxyribonucleotides (DNA) and ribonucleotides (RNA). The nucleic acid may be composed entirely of deoxyribonucleotides, entirely of ribonucleotides, or chimeric mixtures thereof. The monomers are linked by internucleotide phosphodiester bond linkages, and associated counterions, e.g., $H^+$, $NH_4^+$, trialkylammonium, $Mg^{2+}$, and $Na^+$. Nucleic acids typically range in size from a few monomeric units, e.g. 5–40 when they are commonly referred to as oligonucleotides, to several thousands of monomeric units. Whenever an oligonucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

The term "Watson/Crick base-pairing" refers to the hydrogen-bonding base pairing commonly observed in double-stranded DNA. "Attachment site" refers to a site on a moiety, e.g. a chimera or nucleotide, to which is covalently attached a linker. "Linker" refers to one or more atoms used to space one moiety from another, e.g. a label from a nucleotide 5'-triphosphate or the PNA moiety from a DNA moiety in a PNA-DNA chimera.

"PNA-DNA Chimera" refers to an oligomer, or oligomers, comprised of: (i) a contiguous moiety of PNA monomer units and (ii) a contiguous moiety of nucleotide monomer units with an enzymatically-extendable terminus.

"Alkyl" refers to a saturated or unsaturated, branched, straight-chain, branched, or cyclic hydrocarbon radical derived by the removal of one hydrogen atom from a single carbon atom of a parent alkane, alkene, or alkyne. Typical alkyl groups include, but are not limited to, methyl, ethyl, propyl, butyl, and the like. In preferred embodiments, the alkyl groups consist of 1–12 saturated and/or unsaturated carbons.

"Cycloalkyl" refers to a cyclic alkyl radical. Nitrogen atoms with cycloalkyl substituents may form aziridinyl, azetidinyl, pyrrolidinyl, piperidinyl, larger rings, and substituted forms of heterocycles thereof.

"Alkyldiyl" refers to a saturated or unsaturated, branched, straight chain or cyclic hydrocarbon radical of 1–20 carbon atoms, and having two monovalent radical centers derived by the removal of one hydrogen atom from each of two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Alkyldiyl" refers to an unsaturated cyclic or polycyclic hydrocarbon radical having a conjugated resonance electron system and at least two monovalent radical centers derived by the removal of one hydrogen atom from each of two different carbon atoms of a parent aryl compound. Typical alkyldiyl groups include, but are not limited to, radicals derived from benzene, substituted benzene, naphthalene, anthracene, biphenyl, and the like.

"Label" refers to any non-radioisotopic moiety covalently attached to a chimera or nucleotide that is detectable or imparts a desired functionality or property in the primer extension product (Hermanson, 1996). Preferred detectable labels are fluorescent dyes.

"Primer extension" is the enzymatic addition, i.e. polymerization, of monomeric nucleotide units to a primer while the primer is hybridized (annealed) to a template nucleic acid.

PNA-DNA CHIMERA

PNA-DNA chimera are linear oligomers comprised of: 1) a contiguous moiety of PNA monomer units and 2) a contiguous moiety of nucleotides. The two moieties are covalently linked together. The nucleotide moiety of the chimera may be 2'-deoxynucleotides, ribonucleotides, or a mixture thereof. The nucleotide moiety of the chimera has a 3' hydroxyl terminus. The preferred length of the PNA moiety is from 5 to 15 PNA monomer units, reflecting optimum enzymatic activity, hybridization specificity and affinity, economy of synthesis reagents, and ease of chimera synthesis and purification. The length of the DNA moiety is from 3 to 15 nucleotides. The preferred length of the DNA moiety is the shortest sequence which promotes efficient primer extension, i.e. at least three 2'-deoxynucleotides (FIG. 1D).

A preferred form of the PNA moiety is an uncharged backbone of N-(2-aminoethyl)-glycine, a peptide-like, amide-linked unit (Egholm, 1993; Nielsen, 1991) (FIG. 1A). Whenever a PNA sequence is represented as a series of letters, it is understood that the amino terminus is at the left side and the carboxyl terminus is at the right side.

Binding of the PNA moiety to its DNA or RNA complement can occur in either a parallel or anti-parallel orientation of PNA; however, the anti-parallel duplex (where the carboxyl terminus of PNA is aligned with the 5' terminus of DNA, and the amino terminus of PNA is aligned with the 3' terminus of DNA) is typically more stable (Egholm, 1993). The chimera of the present invention are designed such that the PNA moiety anneals in the anti-parallel orientation with the target sequences.

Chimera sequences are typically completely complementary to a portion of the target sequence. However, chimera sequences may contain mixed-base ("redundant" or "degenerate") sites whereby a chimera sample may be a mixture of sequences with one or more sites represented by two or more different nucleobases. The mixed-base site may be located in the PNA or DNA moieties of the oligomer. Mixed-base chimera are mixtures of sequences with varying levels of complementarity to a particular target sequence. Mixed-base chimera may be useful for random priming or where template sequence information is unknown or uncertain.

PNA-DNA chimera can be synthesized using the respective conventional methods of synthesis of PNA oligomers, DNA oligonucleotides, and RNA oligonucleotides. Chimera can be synthesized at a 2–25 μmole scale on commercially available, automated synthesizers, e.g. Expedite, Model 433A and Model 394 Synthesizers (PE Biosystems), and with commercially available reagents (Uhlmann, 1996; Vinayak, 1997; Van der Laan, 1997). In this approach, the chimera can be made continuously, in a single column and on a single synthesizer.

Synthesis of chimera is initiated by detritylation of the 5' dimethoxytrityl (DMT) group of commercially available, high-cross link, non-swelling polystyrene beads packed in a synthesis column. The supports are loaded at 20–30 μmole/gm with 5' DMT deoxynucleosides ($A^{bz}$, $G^{ibu}$, $C^{bz}$, T) linked through the 3' hydroxyl to the support through a base-labile succinate/hydroxymethylbenzoic acid linker (Vinayak, 1997). 5' DMT, 3' cyanoethyl phosphoramidite deoxynucleoside monomers (Beaucage, 1992) are dissolved in dry acetonitrile and delivered concurrently with tetrazole activator and coupled to the support-bound 5' hydroxyl. Coupling is followed by capping with acetic anhydride of unreacted 5' hydroxyls, and iodine oxidation to the pentavalent internucleotide phosphate triester. The DNA synthesis cycle is repeated until the last deoxynucleoside addition, where a 5' monomethoxytrityl (MMT) amino nucleoside phosphoramidite is employed to furnish a 5' amino terminus on the support-bound DNA moiety, for coupling to a PNA monomer at the linkage between DNA and PNA in the chimera. The MMT group is favored in the synthesis of PNA-DNA chimera because of its acid-lability. The MMT group is efficiently and rapidly removed under mild acidic conditions which do not cause depurination or other damage to the chimera.

To initiate synthesis of the PNA moiety, the 5' MMT group is removed with 3% trichloroacetic acid in dichloromethane and the amino group is coupled with a PNA monomer and a coupling reagent. The backbone amino group of the PNA monomers is preferably protected with MMT and the nucleobase exocyclic amines are protected as $A^{bz}$, $G^{ibu}$, and $C^{bz}$ (Breipohl, 1997; Finn, 1996; Will, 1995) Any conventional peptide coupling reagent may be used, but HBTU and HATU are preferred coupling reagents. PNA monomers may be dissolved in 1:1 DMF:acetonitrile to a concentration of about 0.2M. Prior to delivery to the synthesis column, the monomer solution was mixed with an equal volume of 0.2M HBTU (O-benzotriazol-1-yl-N,N,N', N'-tetramethyluronium hexafluorophosphate), also in 1:1 DMF:acetonitrile (Vinayak, 1997). The solution was delivered to the column concurrently with 0.2M diisopropylethylamine in 1:1 DMF:acetonitrile. The synthesis cycles for the PNA and DNA moieties in a chimera are summarized in Table 1 below.

TABLE 1

Synthesis cycles for PNA and DNA moieties of PNA-DNA chimera. Model 394 synthesizer, 2 μmole scale.

| Step | Function | Reagents | PNA Time (sec) | DNA Time (sec) |
|---|---|---|---|---|
| 1 | Detritylation | 3% $CCl_3CO_2H$ in $CH_2Cl_2$ | 60 | 25 |
| 2 | Coupling | PNA: 0.2 M PNA monomer, HBTU, DiPEA in 1:1 DMF:$CH_3CN$ DNA: 0.1 M DNA monomer, 0.5 M tetrazole in $CH_3CN$ | 960 | 25 |
| 3 | Capping | $Ac_2O$, lutidine, N-methylimidazole, THF | 25 | 15 |
| 4 | Oxidation | iodine, pyridine, $H_2O$, THF | not required | 25 |

After synthesis is complete, the amino terminus may be acetylated to minimize migration or cyclization, or reacted as a nucleophile in labelling. The crude chimera is cleaved from the support, and all protecting groups are removed with concentrated ammonium hydroxide at 55° C. for 8–16 hours. The chimera are analyzed and purified by reverse-phase HPLC or polyacrylamide gel electrophoresis (PAGE), analyzed by mass spectroscopy, and quantitated by correlating UV absorbance at 260 nm with mass.

Chimera with a DNA moiety comprising ribonucleotides can be synthesized with the appropriate RNA phosphoramidite nucleosides and/or 5' DMT protected ribonucleotides support (Vinayak, 1994). The 2' hydroxyl of RNA phosphoramidites are typically protected with the tert-butyldimethylsilyl (TBDMS) group and the exocyclic amino groups of the nucleobases are protected as $A^{bz}$, $G^{dmf}$, $C^{bz}$. After synthesis, TBDMS groups are removed with a fluoride reagent, e.g. tetrabutylammonium fluoride in tetrahydrofuran. Otherwise, the synthesis, purification, and analysis methods for ribonucleotide-containing PNA-DNA chimera are virtually the same as for chimera with only 2'-deoxynucleotide containing DNA moieties.

The PNA and DNA moieties are covalently linked together. The linkage may be a direct bond, e.g. an amide bond formed by the amino group at the 5' of a deoxynucleotide and the carboxyl group at the carboxyl terminal of the PNA moiety. The linkage may also comprise one or more units of a non-base pairing moiety such ethyleneoxy, linked to the PNA and DNA moieties by amide or phosphate bonds. Ethyleneoxy linkage units between the PNA and DNA moieties can be installed by coupling reagents such as protected forms of 2-[2-(2-aminoethoxy)ethoxy]acetic acid. The O-linker, 2-[2-(2-aminoethoxy]acetic acid, is coupled as the MMT-amino protected amide-forming carboxylic acid, or phosphoramidite synthons (FIG. 5). One or more O linker units act as a flexible, non-base pairing, linkage between the PNA and DNA moieties. FIG. 6 shows a bis-ethyleneoxy-acetamido linker (6A) and a bis-ethyleneoxy-phosphate linker (6B). Other linkers include alkydiyl, e.g. hexyldiyl (Vinayak, 1997), or 1,4-phenyldiyl (FIG. 5).

NUCLEOTIDE 5'-TRIPHOSPHATES

Nucleotide 5'-triphosphates are substrates of polymerase enzymes and are incorporated into the template/chimera hybrid by internucleotide phosphodiester bond formation between the 3' hydroxyl terminus of the chimera and the 5' hydroxyl of the nucleotide. Further extension by incorporation of more nucleotide 5'-triphosphates requires a new 3' hydroxyl terminus. During primer extension, typically a mixture of nucleotide 5'-triphosphates are present, e.g. dATP, dGTP, dCTP and dTTP. Labelled nucleotides may also be present, for detection, isolation, or immobilization of the extension fragments. Nucleotides which terminate extendability ("terminators" or "terminating nucleotides") may also be present in the mixture, e.g. ddNTP and 2',3'-dehydro-ddNTP. Labelled terminators are particularly useful. Individual concentrations of each nucleotide in the mixture are optimized to promote the desired incorporation rates and achieve the necessary detection levels. Preferred nucleotide 5'-triphosphates of the present invention are shown below in the general structures:

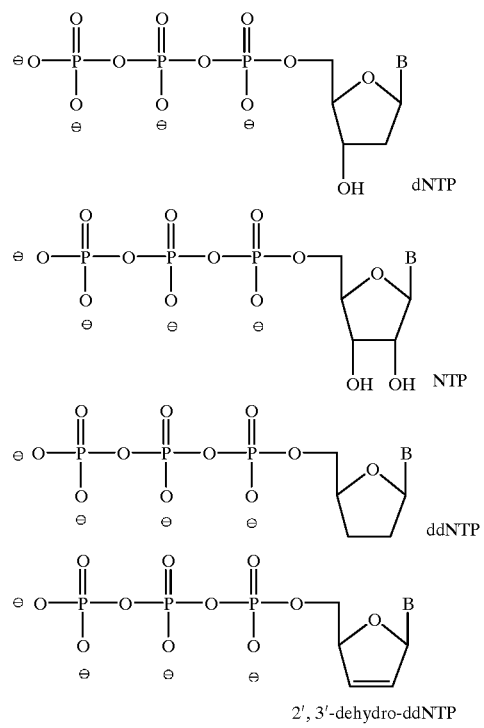

where B is a nucleobase. The 2' position of the ribose sugar moiety may be substituted with 2'-O-alkyl, e.g. methyl, 2'-amino or 2'-halo, e.g. fluoro, chloro, as in the structure:.

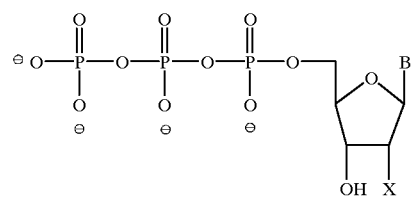

where X is alkoxy, halo, and amino. When B is a purine or a 7-deazapurine, the sugar moiety is attached at the $N^9$-position of the purine or deazapurine, and when B is a pyrimidine, the sugar moiety is attached at the $N^1$-position of the pyrimidine.

Preferably the nucleotide 5'-triphosphate is ATP, dATP, ddATP, CTP, dCTP, ddCTP, GTP, dGTP, ddGTP, UTP, dUTP, TTP, dTTP, ddTTP, 5-methyl-CTP, 5-methyl-dCTP, ITP, dITP, ddITP, 2-amino-ATP, 2-amino-dATP, 7-deaza dATP, 7-deaza ddATP, 5-propynyl dCTP, 7-deaza dGTP, 7-deaza ddGTP, 5-Br-UTP, 5-Br-dUTP, 5-F-UTP, 5-F-dUTP, 5-propynyl-dUTP. Additionally, the α-phosphorus may be substituted with sulfur, as the α-thio-nucleotide 5'-triphosphates (Lee, 1992).

POLYMERASE ENZYMES

A variety of polymerases, e.g. Vent (Kong, 1993), Klenow, Bst, bacteriophage T7 DNA polymerase (Tabor, 1989) and its processivity-enhancing protein partner, *E. coli* thioredoxin, bacteriophage T4 DNA polymerase and its processivity clamp, gp45 protein (Carver, 1997), Taq, and Sequenase conduct primer extension of PNA-DNA chimera. Preferred polymerases include Vent, Klenow and Bst. Polymerases without exo activity (Exo⁻) proof reading function are preferred.

Reverse transcriptase enzymes extend PNA-DNA chimera from RNA templates to make cDNA copies with nucleotide 5'-triphosphates. Preferred reverse transcriptases are from avian myeloblastosis virus (AMV) and murine leukemia virus (MuLV) and HIV.

NUCLEOTIDES

Preferred nucleobases in one or more nucleosides include, but are not limited to, adenine, guanine, cytosine, uracil, thymine, 7-deazaadenine, 7-deazaguanine, C-5-alkyl pyrimidines, 2-thiopyrimidine, 2,6-diaminopurine, C-5-propyne pyrimidine, phenoxazine (Flanagan, 1999), 7-deazapurine, isocytidine, pseudo-isocytidine (Egholm, 1995), isoguanosine, 4(3 H)-pyrimidone, hypoxanthine, and 8-oxopurines (Meyer, 1994).

Preferred sugars in one or more of the nucleosides include, but are not limited to, 2'-deoxyribose, ribose, and 2'- or 3'-ribose modifications where the 2'- or 3'-position may be hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo.

Other preferred sugars include 4'-α-anomeric nucleotides, 1'-α-anomeric nucleotides, and 2'-4'-linked and other "locked", bicyclic sugar modifications (Wengel, 1999).

LABELS

The PNA-DNA chimera or the nucleotide 5'-triphosphates may bear covalently attached non-radioisotopic labels. The chimera and one or more of the nucleotide 5'-triphosphates in a primer extension reaction may bear the same or different labels. Labeling can be accomplished using any one of a large number of known techniques employing known labels, linkages, linking groups, reagents, reaction conditions, and analysis and purification methods. Generally, the linkage linking the dye and nucleotide or chimera should not (i) interfere with primer extension, (ii) inhibit polymerase activity, or (iii) adversely affect the fluorescence properties of the dye, e.g. quenching or bleaching.

PNA-DNA chimera and nucleotide 5'-triphosphates can be labelled at sites including a nucleobase, a sugar, the aminoethylglycine backbone, amino, sulfide, hydroxyl, and carboxyl. Nucleobase label sites include the N-9 or C-8 positions of the purine or deazapurine, and the C-5 position of the pyrimidine. Preferably, the linkage between the label and the chimera or nucleotide 5'-triphosphate are acetylenic amido or alkenic amido linkages (Khan, 1998). Linkers can also comprise alkyldiyl, aryldiyl, or one or more ethyleneoxy units (Rajur, 1997). Typically, a carboxyl group on the label is activated by forming an active ester, e.g. N-hydroxysuccinimide (NHS) ester and reacted with an amino group on the alkynylamino- or alkenylamino-derivatized chimera or nucleotide.

Labelled 2',3'-dideoxynucleotides, ddNTP, find particular application as chain terminating agents, or "terminators" in the Sanger-type DNA sequencing method of primer extension, and for sizing/identification and analysis. Labelled deoxynucleotides, dNTP, find particular application as means for labelling primer extension products, e.g. in the polymerase chain reaction (Mullis, 1987).

A preferred class of labels provide a signal for detection of labelled extension products by fluorescence, chemiluminescence, and electrochemical luminescence (Kricka, 1992). Particularly preferred chemiluminescent labels are 1,2-dioxetane compounds (Bronstein, 1994; Bronstein, 1990). Fluorescent dyes useful for labelling chimera and nucleotide 5'-triphosphates include fluoresceins (Menchen, 1993), rhodamines (Bergot, 1994), cyanines (Lee, 1998 (Ser. No. 09/012,525); Kubista, 1997), and metal porphyrin complexes (Stanton, 1988).

Figure 2:
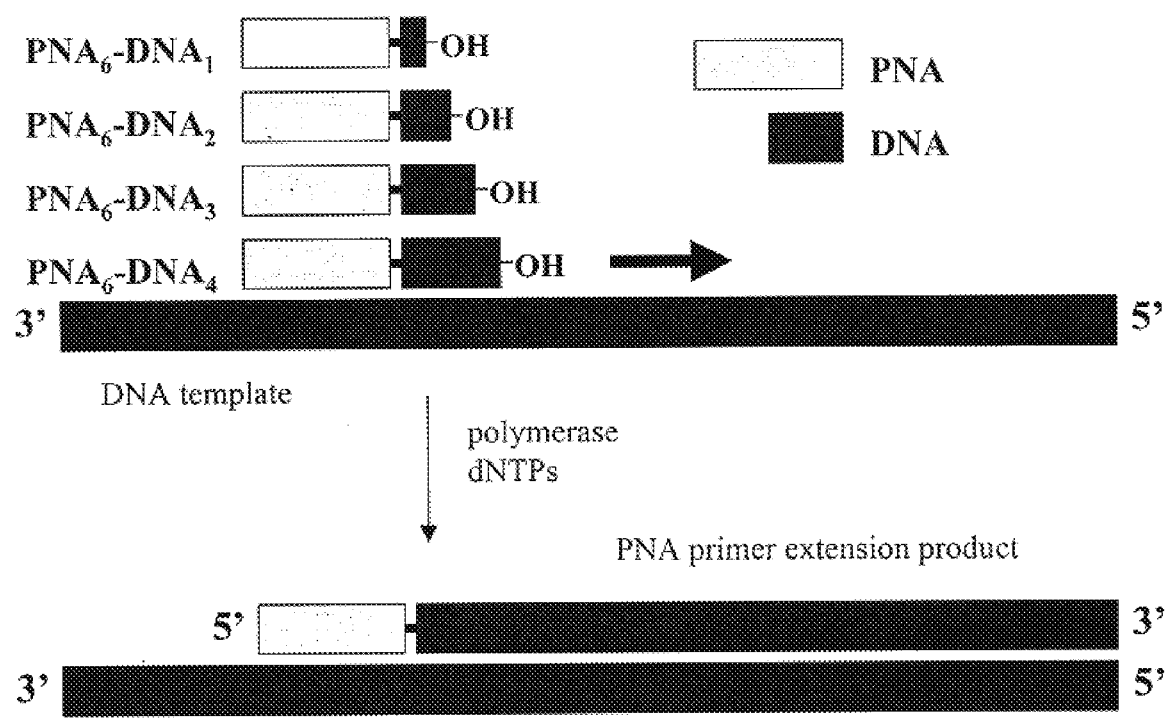
FIG. 2 Schematic of extension of PNA-DNA chimera on a template nucleic acid.
Figure 3B:
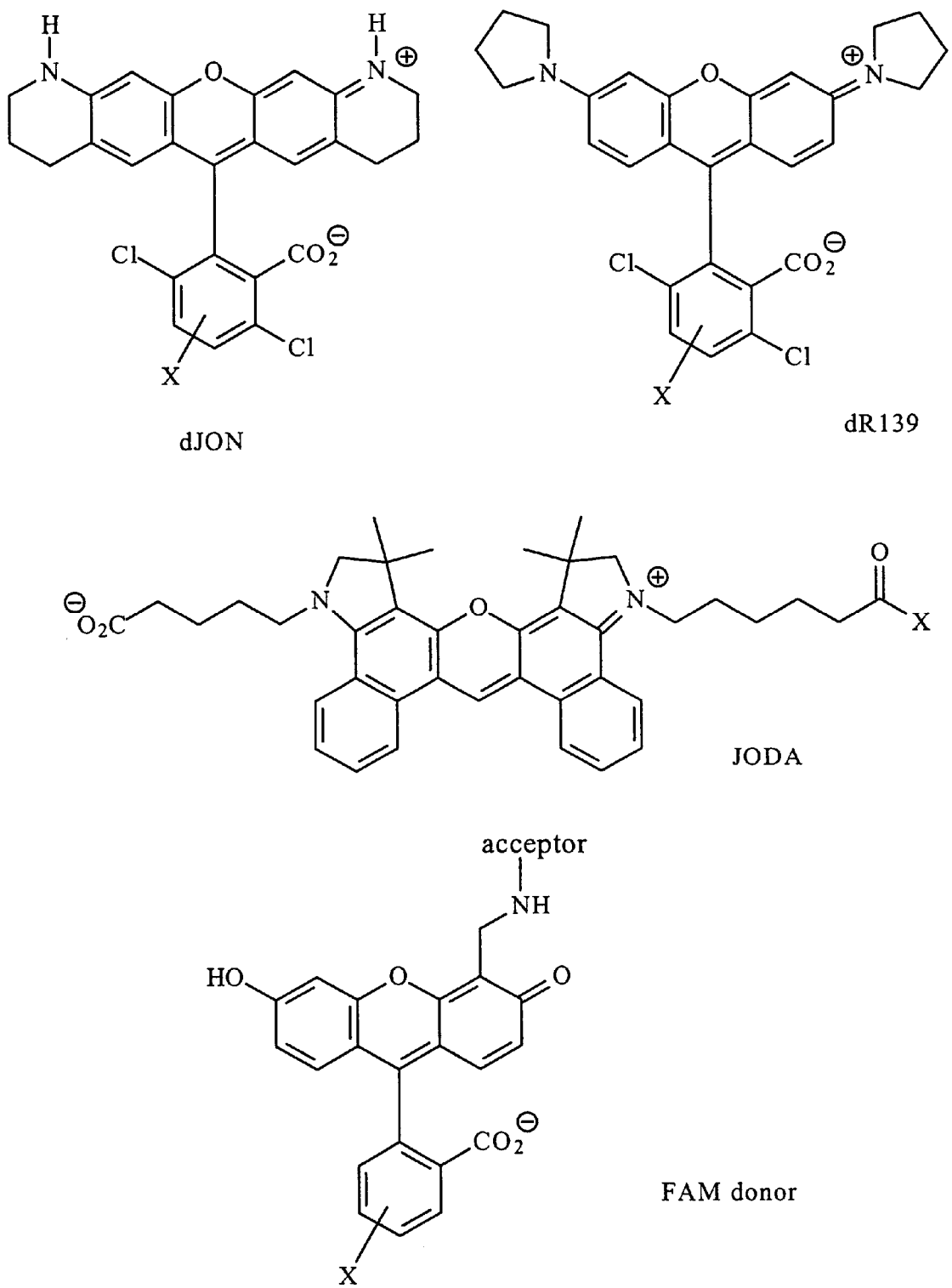

Examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluoresccin (NED), 2'-chloro-7'-phenyl-1,4-dichloro-6-carboxyfluorescein (VIC), and (JODA) (FIGS. 3A–3B). The 5-carboxyl, and other regio-isomers, may also have useful detection properties. Fluorescein and rhodamine dyes with 1,4-dichloro substituents (bottom ring as shown) are especially preferred.

Another preferred class of labels include fluorescence quenchers. The emission spectra of a quencher overlaps with a proximal intramolecular or intermolecular fluorescent dye such that the fluorescence of the fluorescent dye is substantially diminished, or quenched, by the phenomena of fluorescence resonance energy transfer "FRET" (Clegg, 1992).

Particularly preferred quenchers include but are not limited to (i) rhodamine fluorescent dyes selected from the group consisting of tetramethyl-6-carboxyrhodamine (TAMRA), tetrapropano-6-carboxyrhodamine (ROX), and (ii) DABSYL, DABCYL, cyanine dyes including nitrothiazole blue (NTB), anthraquinone, malachite green, nitrothiazole,and nitroimidazole compounds and the like (FIG. 4). Nitro-substituted forms of quenchers are especially preferred.

Energy-transfer dyes are a preferred class of oligonucleotide labels. An energy-transfer dye label includes a donor dye linked to an acceptor dye (Lee, 1998, U.S. Pat. No. 5,800,996), or an intramolecular FRET pair (Livak, 1998; Livak, 1996; Tyagi, 1996). Light, e.g. from a laser, at a first wavelength is absorbed by a donor dye, e.g. FAM. The donor dye emits excitation energy absorbed by the acceptor dye. The acceptor dye fluoresces at a second wavelength, with an emission maximum preferably about 100 nm greater than the absorbance maximum of the donor dye.

The donor dye and acceptor dye of an energy-transfer label may be directly attached by a linkage such as:

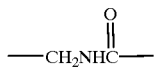

formed from an aminomethyl group at the 4' or 5' positions of the donor dye, e.g. FAM, and a 5- or 6-carboxyl group of the acceptor dye (FIG. 3B). Other rigid and non-rigid linkers may be useful.

Another preferred class of labels serve to effect the separation or immobilization of labelled primer extension products by specific or non-specific capture means, e.g. biotin, 2,4-dinitrophenyl (DNP), and digoxigenin (Andrus, 1995).

Another preferred class of labels are electrophoretic mobility modifiers, e.g. polyethyleneoxy (PEO) units. The PEO label may be comprised of charged groups, such as phosphodiester to impart charge and increase electrophoretic mobility (velocity). The PEO label may be uncharged and act to retard electrophoretic mobility. Such modifiers may serve to influence or normalize the electrophoretic velocity of a set of labelled primer extension products during analysis, e.g. by fluorescent detection, to improve resolution and separation (Grossman, 1995) Another preferred class of labels, referred to herein as hybridization-stabilizers, include but are not limited to minor groove binders, intercalators, polycations, such as poly-lysine and speimine, and cross-linking functional groups. Hybridization-stabilizers may increase the stability of base-pairing, i.e. affinity, or the rate of hybridization (Corey, 1995) of the chimera and the template. Hybridization-stabilizers serve to increase the specificity of base-pairing, exemplified by large differences in Tm between perfectly complementary oligonucleotide and target sequences and where the resulting duplex contains one or more mismatches of Watson/Crick base-pairing (Blackburn, 1996, pp. 15–81 and 337–46). Preferred minor groove binders include Hoechst 33258 (Rajur, 1997), CDPI$_{1-3}$ (Kutyavin, 1996), MGB1 (Gong, 1997),

PRIMER EXTENSION

Primer extension is initiated at the template site where a primer anneals. One or more different nucleotide 5'-triphosphates may be present in the reaction mixture such that the complementary nucleotide is incorporated by a polymerase enzyme according the template sequence. Extension of the chimera continues until nucleotides are depleted, the enzyme is no longer functional, or termination occurs by incorporation of a terminating nucleotide that will not support continued DNA elongation. Chain-terminating nucleotides are typically 2',3'-dideoxynucleotide 5'-triphosphates (ddNTP), which lack the 3'—OH group necessary for 3' to 5' DNA chain elongation. Other terminating nucleotides include 2',3'-dideoxy-dehydro; 2'-acetyl; 2'-deoxy, halo; and other 2'-substituted nucleotide 5'-triphosphates.

In general, the reaction conditions for primer extension involve an appropriate buffering system to maintain a constant pH, a divalent cation, a PNA-DNA chimera primer, a template nucleic acid, nucleotide 5'-triphosphates, and a polymerase. Additional primer extension reagents, such as reducing agents, monovalent cations, or detergents may be added to enhance the reaction rate, fidelity, or other parameters. Different polymerases may have different optimal pH values or ion concentrations.

Klenow without exo activity (exo-) extended PNA-DNA chimera primers comprised of six contiguous PNA monomers and three or four contiguous 2'-deoxynucleotides (FIGS. 7 and 8). The same chimera were not extended to give full length product by AmpliTaq FS® polymerase (FIG. 7 middle panel). PNA-DNA chimera with 0–2 2'-deoxynucleotides were not extended by either enzyme (FIGS. 7 and 8). The identity of the full length 29 nt (PNA$_6$DNA$_{23}$) extension product from lane 6 in FIG. 7 was confirmed by MALDI-TOF mass spectroscopy (FIG. 12).

The specificity advantage of PNA-DNA chimera primers relative to DNA primers is shown in FIG. 9. When various primers were extended with Klenow (exo-) or Bst polymerases on a 38 nt DNA template (SEQ. ID NO. 8) with perfect complementarity (FIG. 10), chimera primers with three (6/3) and four (6/4) 2'-deoxynucleotides were extended, as well as the corresponding all-DNA 9 nt primer (0/9) The all-DNA hexamer (0/6) showed a weaker band under the SYBR-Green staining detection. The all-DNA extension products from 0/6 and 0/9 primers migrated faster than the PNA-DNA extension products from 6/3 and 6/4. However, when the template contained a mismatch either across from the 2nd base (SEQ. ID NO. 12) or 4th base (SEQ. ID NO. 13) from the PNA-DNA linkage site, the PNA-DNA chimera did not extend (FIG. 11). The all-DNA 9 nt primer (0/9) did extend, showing a band of near equal intensity to the perfect match extension product. Thus while the all-DNA primer showed little specificity, i.e. sequence discrimination of a mismatch, the corresponding PNA-DNA chimera showed absolute specificity within the detection limits of the experiment. The results of this experiment follows other reports that PNA probes are more sensitive to mismatches than DNA probes (Kyger, 1998).

Labeled primer extension products, "fragments", are generated through template-directed enzymatic synthesis using labeled chimera primers or nucleotides. The fragments can be separated by a size-dependent process, e.g., electrophoresis or chromatography; and the separated fragments detected, e.g., by laser-induced fluorescence. In a preferred fragment analysis method, Sanger-type sequencing, a chimera primer is extended by a DNA polymerase in vitro using a single-stranded or double-stranded DNA template whose sequence is to be determined. Extension is initiated at a defined site based on where a chimera anneals to the template. The extension reaction is terminated by incorporation of a nucleotide that will not support continued DNA elongation, i.e. a terminating nucleotide. When optimized concentrations of dNTP and terminating nucleotides are used, enzyme-catalyzed polymerization (extension) will be terminated in a fraction of the population of chains at each site where the terminating nucleotide is incorporated such that a nested set of primer extension fragments result. If fluorescent dye-labeled chimera primers or labeled terminating nucleotides are used for each reaction, the sequence information can be detected by fluorescence after separation by high-resolution electrophoresis (Smith, 1998). Each of the four possible terminating nucleotides (A,G,C,T) may be present in the extension reaction and bear a different fluorescent dye which are spectrally resolvable (Bergot, 1994).

"Mini-sequencing" is another application involving incorporation of terminating nucleotides in single-base extension assays where PNA-DNA chimera may be useful to determine the identity, presence, or absence of a nucleotide base at a specific position in a nucleic acid target of interest (Goelet, 1999; Syvanen, 1990). Genotype determination based on identification of different alleles is based on single nucleotide polymorphisms (SNP). SNP can be detected by ddNTP incorporation from PNA-DNA chimera primers annealed immediately adjacent to the 3' of the SNP site of the target nucleic acid sequence to be determined, and detection of the extension products by MALDI-TOF mass spectroscopy (FIG. 14). The mass difference resulting from incorporation of different dideoxynucleotides can be accurately determined by mass spectrometry. More than one chimera primer, each with a different sequence and mass, allows detection of multiple SNP in a single tube or reaction, by analyzing the mass spectra of the extension products.

Primed in situ labeling (PRINS) is a molecular cytogenetic technique that combines the high sensitivity of PCR with the cellular or chromosome localization of fluorescent signals provided by in situ hybridization. PRINS can be conducted by annealing unlabelled PNA-DNA chimera primers to complementary target sequences, followed by a DNA polymerase extension in the presence of labelled dNTP. Preferably the labels are fluorescent dyes, so that the extension products can be detected and/or measured by fluorescence detection (Koch, 1991).

In one embodiment of the invention, the PNA-DNA chimera is immobilized to a solid substrate through an ionic attraction, affinity/receptor interaction, or covalent linkage. The solid substrate may be particles, beads, membranes, frits, slides, plates, micromachined chips, alkanethiol-gold layers, non-porous surfaces, or other polynucleotide-immobilizing media. The solid substrate material may be polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of such.

In this embodiment, the chimera may be physically manipulated by automated means, e.g. assembling an addressable array of multiple chimera, prior to primer-extension. Primer extension reagents, including template, nucleotide 5'-triphosphates, and polymerase may be delivered in solution to the location, well, vessel, or spot of the solid substrate bearing the chimera. Primer extension may be conducted in such a heterogeneous media. After extension is complete, all reagents in solution may be conveniently removed by filtration, aspiration, centrifugation, sedimentation, decanting, or magnetic pull-out of magnetic particles. Alternatively, primer extension products may be detached or released from the solid substrates in a pure state by selective chemical, thermal, or enzymatic cleavage.

In another and similar embodiment, a template nucleic acid may be immobilized on a solid substrate in the same configurations and materials (supra). Primer extension reagents including PNA-DNA chimera, nucleotide 5'-triphosphates, and polymerase may be delivered in solution to the immobilized template and primer extension conducted in a heterogeneous media. Primer extension products can be conveniently separate from the template and detected.

EXAMPLES

The invention will be further clarified by a consideration of the following examples, which are intended to be purely exemplary of the present invention and not to limit its scope in any way.

Example 1

Labelling of PNA-DNA Chimera

TAMRA and NTB labeling:

Labeling is performed with 5 mg of NHS ester of TAMRA or NTB dissolved in 100 µl DMF or NMP and 10 µl DIEA added to the support bound PNA-DNA chimera and allowed to react for 2 to 18 hours (typically overnight). The support is washed following the labeling with DMF and subsequently DCM prior to cleavage.

CDPI labeling:

$CDPI_3$ is attached to the chimera by three consecutive couplings of Fmoc-CDPI (Lukhtanov, 1995) to give $CDPI_3$-labelled PNA-DNA chimera. The CDPI monomer unit, 1,2-dihydro-(3H)-pyrrolo[3,2-e]indole-7-carboxylate, protected with Fmoc (5 mg, 0.012 mmole) is dissolved in 100 µl NMP and activated by 0.95 equivalents HATU (0.2M in DMF) and 2 equivalents DIEA (0.4M in DMF). After one hour at room temperature, the activated Fmoc-CDPI solution is added to the support bound chimera and allowed to couple for another hour at room temperature. The resin is washed following the coupling with 20 ml DMF. The Fmoc is removed by treatment of the resin support with 1:4 piperidine:DMF for 10 minutes at room temperature. This coupling and deprotection cycle is repeated two additional times for a total of 3 manual couplings to give $CDPI_3$-labelled PNA-DNA chimera.

Example 2

Primer Extension from DNA 38 mer Template with Klenow, Taq FS, and No Enzyme Control

```
    Ac-TAGTTC-t            (SEQ. ID NO.2)

Ac-TAGTTC-ta           (SEQ. ID NO.3)

Ac-TAGTTC-tag          (SEQ. ID NO.4)

Ac-TAGTTC-taga         (SEQ. ID NO.5)

Ac-TAGTTCT-ag          (SEQ. ID NO.9)

Ac-TAGTTCT-aga         (SEQ. D NO.10)

Ac-TAGTTCT-agac        (SEQ.ID NO.11)
UPPER CASE = PNA, lower case = DNA. All chimera
above have amide linkage. Amino terminus of PNA is
acetylated (Ac).
```

2.1. Annealing of Primers and Templates

PNA-DNA chimera, PNA, and DNA primers (FIGS. 7–11) were annealed to the synthetic 38-mer DNA oligonucleotide templates:

```
5' CGC TCA ACA CAT AGC ATG GTC TAG AAC TAA GCC TGG AA   (SEQ. ID. NO. 8)
3'

5' CGC TCA ACA CAT AGC ATG GTC CAG AAC TAA GCC TGG AA   (SEQ. ID. NO. 12)
3'

5' CGC TCA ACA CAT AGC ATG GCC TAG AAC TAA GCC TGG AA   (SEQ. ID. NO. 13)
3'
``` where bold, underlined bases indicate mismatch bases. The mixtures were heated to 95° C. and slowly cooled to 37° C.

during one hour in a thermocycler instrument (PE GeneAmp PCR System 9700, PE Biosystems).

2.2. Polymerase Extension Reaction with Non-thermostable DNA polymerases

PNA-DNA chimera and DNA primers were extended from their respective 3'—OH ends for 2 to 16 h at 37° C. with 2.5–50 units of DNA polymerase, e.g. Kienow, T4, or Bst DNA polymerase, and primer-extension buffer in 25 to 100 µl total volume. In the case of Klenow, for example, 0.1 to 1 mM each nucleotide-5'-triphosphate and 1×EcoPol buffer containing 10 mM Tris-HCl (pH 7.5), 5 mM MgCl$_2$, and 7.5 mM dithiothreitol were added into each reaction.

2.3. Primer Extension Reaction with Thermostable DNA Polymerases

A total of 50 µl of primer extension mixture generally includes 2.5 to 25 U thermostable polymerase (i.e. AmpliTaq Gold), 1×PCR buffer II containing 50 mM KCl, 10 mM Tris-HCl, pH 8.3, 200 to 500 µM of each dNTP, and 2 to 4 mM of MgCl$_2$. Primer extension is performed for 25–40 rounds of thermal cycling in a program (10 min at 95° C. once, then 0.5 min at 95° C., 1 to 5 min at 37 to 67° C., 1 to 10 min at 60 to 72° C. for cycling).

2.4. Electrophoresis and Visualization

After incubation, reaction product was placed on ice or at 4° C. for a short period. Typically, 5 to 25 pmol of the extended product was mixed with a final concentration of 1×loading buffer (45 mM Tris base, 45 mM boric acid, 0.4 mM EDTA, 3% Ficoll, 0.02% bromophenol blue, 0.02% xylene cyanol) and denatured at 95° C. for 10 to 20 min. The sample is loaded into a 10 to 15% denaturing PAGE gel and run in 1×TBE (89 mM Tris base, 89 mM boric acid, 2 mM EDTA, pH 8.3) at 100 to 160 V, 70° C. for 25 to 60 min. The extended product was visualized by staining the gel with SYBR-Green (Molecular Probes, Eugene, Oreg.) in a volume of 40 to 120 ml in 1×TBE for 10 to 30 min. The image was captured in an ChemImaging 2000 gel documentation system.

In the case of Klenow polymerase, for example, reaction conditions are 25° C. and 10 mM Tris-HCl pH 7.5, 5 mM MgCl$_2$, 7.5 mM dithiothreitol, 1 mM each nucleotide 5'-triphosphate, 0.1 to 100 pmoles chimera, 0.1 to 100 pmoles template, and 0.1 to 10 units Klenow enzyme in 5 to 500 µl total volume.

A Taq polymerase primer extension reaction may be conducted at 72–80° C. and contain 10 mM KCl, 20 mM Tris-HCl pH 8.8, 10 mM (NH4)$_2$SO$_4$, 2 mM MgSO$_4$, 0.1% Triton X-100 detergent, 1 mM each nucleotide 5'-triphosphate, 0.1 to 100 pmoles chimera, 0.1 to 100 pmoles template, and 0.1 to 10 units Taq polymerase enzyme in 5 to 500 µl total volume.

2.5. MALDI-TOF Analysis

Mass spectra is acquired on a MALDI-TOF MS (Voyager DE) workstation. Desalted samples are mixed 1:1 with matrix solution consisting of 50 mg/ml 3-hydroxy picolinic acid, 50 mM ammonium citrate, and 30% acetonitrile, and is spotted onto a sample plate. Time-of-flight data from 20 to 50 individual laser pulses are recorded and averaged on a transient digitizer, after which the averaged spectra are automatically converted to mass by data processing software.

Example 3

RT-PCR Murine Xist Gene

| | |
|---|---|
| P1 | Ac-TA GGT CCC GGC ttta (SEQ. ID NO. 14) |
| P2 | Ac- TA GGT CCC GGC t (SEQ. ID NO. 15) |
| D1 | AAC AGT TA GGT CCC GGC TTT (SEQ. ID NO. 16) |
| D2 | ACT GGG ATG CAA AGA GCA TT (SEQ. ID NO. 17) |
| D3 | TGC CTG GGA TAA AAG CAA AG (SEQ. ID NO. 18) |

Total RNA was isolated by using the guanidinium thiocyanate method from kidneys of male and female mice (Chirgwin, 1979). Reverse transcription was conducted on 0.5 to 1.5 µg total RNA samples with 10 pmoles of Xist-specific primers including DNA RT primer D1 or PNA-DNA chimera RT primers P1 and P2, respectively, 0.2–1 mM each of dATP, dGTP, dCTP, dTTP, 10 to 20 µl RT reaction buffer (10 mM Tris-HCl, pH 8.3, 90 mM KCl), and 2 to 10 U recombinant *Thermus thermophilus* (rTth) DNA polymerase. The solution was incubated for 10 min at 65° C. followed by 60 min at 60 ° C. The samples were PCR amplified (30s at 94° C., 30s at 55° C., and 30s at 65° C.) in 1×chelating buffer [5% (v/v) glycerol, 10 mM Tris-HCl, pH 8.3, 0.05% Tween 20, 0.75 mM EDTA] with 2 to 10 U rTth DNA polymerase and 20 pmoles of each primer (D2 and D3). PCR products were separated and analyzed by 1 to 3% agarose gel electrophoresis with SYBR-Green staining (FIG. 13). The P2 PNA-DNA chimera, with four 2'-deoxynucleotides, was effective in producing an amplifiable copy of mouse Xist gene, whereas the P1 chimera, with only one 2'-deoxynucleotide, was not.

In the case of M-MuLV reverse transcriptase, altered reaction conditions were 37° C. and 50 mM Tris-HCl pH 8.3, 8 mM MgCl$_2$, 10 mM dithiothreitol, 1 mM each dNTP, 0.1 to 100 pmoles chimera primer, 0.1 to 100 pmoles template, and 0.1 to 10 U M-MuLV enzyme in 5 to 500 µl total volume.

Example 4

SNP Detection

A nested PCR is generally recommended for genomic targets. Briefly, 5 pmoles PCR primers flanking the target sequences are subject to 10 rounds of thermal cycling (30s at 94° C., 30s at 55–70° C.) in 25 l of reaction buffer comprising 1×Taq buffer described previously, 400 µM of each dNTP, 4 mM MgCl$_2$, 20–50 ng human genomic DNA, 0.5 to 5 U Taq DNA polymerase or other thermostable enzymes. After 50 pmoles specific pairs of DNA primers are added, the mixture is thermal cycled for an additional 15–20 rounds to amplify all loci.

Multiplex SNP Extension Assay

To 20 µl PCR mixture is added 1 U each of shrimp alkaline phosphatase and 10 U exonuclease I. The mixture is incubated for 15 min at 37° C. followed by 15 min at 85° C.

Then, 20 μl of a mixture containing 25–100 μM each ddNTP, 2 mM $MgCl_2$, 1 to 5 U Taq polymerase, 1×PCR buffer, and 20–50 pmoles of each PNA-DNA chimera primer is added subsequently. The resultant mixture is subjected to 25–35 rounds of thermal cycling (30s at 94° C., 30s at 37 to 67° C., 20–90s at 70° C.). Desalting 10 to 50 μl of the reaction mixture is performed by absorption/elution using ZipTip or 96-well plate packed with small quantities of POROS 50 R1, R2, or R3 chromatography media.

Example 5

Fluorescence Detection of Primer Extension of PNA-DNA Chimera with TAMRA-dUTP

PNA-DNA chimera primer (SEQ. ID NO. 4) was extended with 3 different mixtures of nucleotides (a., b., c.) after annealing to 5' biotin DNA 38 nt template (SEQ. ID NO. 8) with a variety of polymerases (FIG. 15). The biotin label serves to enable capture affinity of duplex extension products or recovery of template by binding to avidin, e.g. immobilized strepavidin. Polyacrylamide (15%) gel electrophoresis under denaturing conditions with fluorescence detection (no staining) showed only the expected fluorescence in reactions (b) with TAMRA-dUTP. The dark bands at 15 and 20 bp correspond to TAMRA-dUTP and a dimer artifact, respectively. Full length extension product is apparent in reactions employing (left to right) Klenow, AmpliTaq, TaqGold, Vent, Stoffel fragment, and Sequenase as a faint band migrating at the rate of a 30 bp DNA duplex. These results demonstrate the incorporation of a labelled nucleotide, e.g. TAMRA-dUTP, with a range of polymerases.

Example 6

Primed in situ Labeling (PRINS)—Chromosome Labelling by PNA-DNA Chimera Primer Extension with TAMRA-dUTP A reaction mixture containing 1–3 μM PNA-DNA chimera primer, 100 to 200 μM of each dATP, dCTP, dGTP, 20 μM dTTP, 20 μM of FAM-12-dUTP, 50 mM KCl, 10 mM Tris-HCl, pH 8.3, 1–5 mM $MgCl_2$, 0.01% bovine serum albumin, and 2 to 10 U Taq DNA polymerase is prepared to a final volume of 50 μl. A total of 20 to 30 μl reaction mixture is placed on each slide. The slide is incubated on a programmable temperature cycler (PE Ampli2000). The program consists of 15–30 min at 50–65° C. for annealing and 30 to 120 min at 72° C. for extension. The reaction is stopped by immersing the slides in 50 mM NaCl, 50 mM EDTA, pH 8 at 72° C. for 5 min. After incubation, the slides are washed three times with 70% formamide/10 mM Tris pH 7.2 for 10 min and with 0.05 M Tris/0.15 M NaCl/0.05% Tween-20 pH 7.5 for 5 min. The slides are then dehydrated in an ethanol series and air dried in the dark. Chromosomes are counterstained with either 0.1 μg/ml of 4,6-diamidino-2-phenylindole-dehydrochloride (DAPI) in anti fade or 0.6 μg/ml of propidium iodide (Oncor, Gaitherburg, Md.).

Example 7

DNA Sequencing with PNA-DNA Chimera Primer and Fluorescent Dye-labelled Terminating Nucleotide 5'-triphosphates Rhodamine labelled, 2',3'-dideoxynucleotides and PNA-DNA chimera primer:

```
Ac-ACG ACG GCC agt 3'        (SEQ. ID NO. 19)
``` are used to label DNA fragments in chain termination sequencing on an Applied Biosystems 3 10 Genetic Analyzer. The template nucleic acid, pGEM, (0.4 pmoles) was annealed with the primer (0.8 pmoles) and primer-extension reagents comprising 2 μl buffer (400 mM Tris-HCl, 10 mM $MgCl_2$, pH 9.0.), 2 μl of a deoxynucleotide/labelled dideoxynucleotide mixture, and 2 μl of AmpliTaq DNA polymerase FS enzyme (5 Units/μl). The FS enzyme is a recombinant *Thermus aquaticus* DNA polymerase having two point mutations—G46D and F667Y. The protocol is provided in the ABI PRISM™ Dye Terminator Cycle Sequencing Core Kit Manual (PE Biosystems). The reaction is then thermocycled using the following exemplary program: denaturation at 98° C. for 5 s followed by repeated cycles of: 96° C. for 5 s, 55° C. for 40 s, and 68° C. for 1 min. This cycle is repeated approximately 15 times.

The nucleotide mixture consists of dNTP: 2 mM each dATP, dCTP, 7-deaza-dGTP and dTTP, and labelled ddNTP: 9.0 μM 5R6G-ddATP, 2.7 μM 5R110-ddGTP, 54 μM 6ROX-ddCTP, and 216 μM 6TMR-ddTTP.

The primer extension sequencing reactions can be conducted in 0.5 ml tubes adapted for a thermal cycling reaction period in a thermal cycler, e.g. Perkin-Elmer 480 DNA Thermal Cycler (PE Biosystems). Reaction volumes may be 20 μl, including 15 μl of the above reaction premix, a variable amount of fluorescent dye-labeled terminator, and a sufficient volume of water to bring the total reaction volume up to 20 μL. From 1 to 1000 pmol of the dye terminator can be added to each reaction. Mineral oil (30 μl) is added to the top of each reaction to prevent evaporation. Reactions are thermocycled as follows: 96° C. for 30 sec, 50° C. for 15 sec, and 60° C. for 4 min, for 25 cycles; by a 4° C. hold cycle.

Reactions are purified on Centri-Sep spin columns according to manufacturer's instructions (Princeton Separations). After the column is hydrated with 0.8 mL deionized water for at least 30 minutes at room temperature, inspected to determine that no bubbles are trapped in the gel material, the upper and lower end caps of the column are removed, and the column is allowed to drain by gravity. The column is then inserted into the wash tubes provided in the kit and centrifuged in a variable speed microcentrifuge at 13,000×g for 2 minutes, removed from the wash tube, and inserted into a sample collection tube. The reaction mixture is carefully removed from under the oil and loaded onto the gel material. Loaded columns are centrifuged to elute the samples which are then dried in a vacuum centrifuge.

Prior to loading onto a sequencing gel, the dried samples are resuspended in 25 μl of Template Suppression Reagent (PE Biosystems), vortexed, heated to 95° C. for 2 minutes, cooled on ice, vortexed again, and centrifuged. A 10 μl aliquot of the resuspended sample is transferred to sample vials for electrophoresis on the PE ABI PRISM™ 310 Genetic Analyzer (PE Biosystems) with sieving polymers including nucleic acid denaturants, and capillaries specially adapted for DNA sequence analysis. Samples are electrokinetically injected onto the capillary for 30 s at 2.5 kV, and run for 2 hr at 10 to 12.2 kV with the outside wall of the capillary maintained at 42° C.

All publications and patent applications are herein incorporated by reference to the same extent as if each individual publication or patent application was specifically and individually indicated to be incorporated by reference.

Although only a few embodiments have been described in detail above, those having ordinary skill in the relevant arts will clearly understand that many modifications are possible in the preferred embodiment without departing from the teachings thereof. All such modifications are intended to be encompassed within the following claims.

REFERENCES

Andrus, A. "Chemical methods for 5' non-isotopic labelling of PCR probes and primers" (1995) in PCR 2: *A Practical Approach*, Oxford University Press, Oxford, pp. 39–54.

Beaucage, S. and Iyer, R. "Advances in the synthesis of oligonucleotides by the phosphoramidite approach", Tetrahedron 48:2223–2311 (1992).

Bergot, B., Chakerian, V., Connell, C., Eadie, J., Fung, S., Hershey, N., Lee, L., Menchen, S. and Woo, S. "Spectrally resolvable rhodamine dyes for nucleic acid sequence determination", U.S. Pat. No. 5,366,860, issued Nov. 22, 1994.

Blackburn, G. and Gait, M. Eds. "DNA and RNA structure" in *Nucleic Acids in Chemistry and Biology*, $2^{nd}$ Edition, (1996) Oxford University Press.

Breipohl, G., Will, D. W., Peyman, A. & Uhlmann, E. "Novel synthetic routes to PNA monomers and PNA-DNA linker molecules" Tetrahedron 53:14671–86 (1997).

Bronstein, I. and Voyta, J., "Methods of using chemiluminescent 1,2-dioxetanes" U.S. Pat. No. 4,931,223, issued Jun. 5, 1990.

Bronstein, K., Fortin, J., Stanley, P., Stewart, G. and Kricka, L. "Chemiluminescent and bioluminescent reporter gene assays", Anal. Biochemistry 219:169–81 (1994).

Buchardt, O., Egholm, M., Nielsen, P., and Berg, R. "Peptide Nucleic Acids", WO 92/20702, Intl. Pub. Date Nov. 26, 1992.

Caruthers, M. and Beaucage, S. "Phosphoramidite compounds and processes", U.S. Pat. No. 4,415,732, issued Nov. 15, 1983.

Caruthers, M. and Matteucci, M. "Process for preparing polynucleotides", U.S. Pat. No. 4,458,066, issued July 3, 1984.

Chirgwin, J. M., Przybyla, A. E., MacDonald, R. J., and Rutter, W. J., Biochemistry 18:5294–9 (1979).

Clegg, R., "Fluorescence resonance energy transfer and nucleic acids", Meth. Enzymol., 211:353–388 (1992).

Corey, D. "48000-fold Acceleration of hybridization by chemically modified oligonucleotides" J. Amer. Chem. Soc. 117:9373–74 (1995).

Demers, D. "Method for enhancing amplification in the polymerase chain reaction employing peptide nucleic acid (PNA)" U.S. Pat. No. 5,629,178, issued May 13, 1997.

Egholm, M., Buchardt, O., Christensen, L., Behrens, C., Freier, S., Driver, D., Berg, R. and Kim, S. "PNA hybridizes to complementary oligonucleotides obeying the Watson-Crick hydrogen bonding rules", Nature 365:566–68 (1993).

Egholm, M., Christensen, L., Dueholm, K., Buchardt, O., Coull, J., and Nielsen, P. "Efficient pH-independent sequence-specific DNA binding by pseudoisocytosine-containing bis-PNA", Nucleic Acids Res. 23:217–22 (1995).

Finn, P. J., Gibson, N. J., Fallon, R., Hamilton, A. & Brown, T. "Synthesis and properties of DNA-PNA Chimeric oligomers" Nucleic Acids Research 24:3357–63 (1996).

Flanagan, W., Wagner, R., Grant, D., Lin, K. and Matteucci, M. "Cellular penetration and antisense activity by a phenoxazine-substituted heptanucleotide", Nature Biotech. 17:48–52 (1999).

Goelet, P., Knapp, M., and Anderson, S. "Method for determining nucleotide identity through primer extension" U.S. Pat. No. 5,888,819, issued Mar. 30, 1999.

Gong, B. and Yan, Y. "New DNA minor-groove binding molecules with high sequence-selectivities and binding affinities", Biochem. and Biophys. Res. Comm. 240:557–60 (1997).

Grossman, P., Fung, S., Menchen, S., Woo, S. and Winn-Deen, E. "Probe composition containing a binding domain and polymer chain and methods of use" U.S. Pat. No. 5,470,705, issued Nov. 28, 1995.

Hermanson, G. in *Bioconjugate Techniques* (1996) Academic Press, San Diego, pp. 40–55, 643–671.

Khan, S., Menchen, S., Rosenblum, B. "Substituted propargylethoxyamido nucleosides, oligonucleotides and methods for using same", U.S. Pat. No. 5,770,716, issued Jun. 23, 1998, and "Propargylethoxyamino nucleotides", U.S. Pat. No. 5,821,356, issued Oct. 13, 1998

Koch, J., Hindkjaer, J., Mogensen, J., Kolvraa, S., and Bolund, L. Genet. Anal. Tech. Appl. 8:171–78 (1991).

Kong, H., Kucera, R., Jack, W. "Characterization of a DNA polymerase from the hyperthermophile archaea Theimococcus litoralis. Vent DNA polymerase, steady state kinetics, thermal stability, processivity, strand displacement, and exonuclease activities" J. Biol. Chem. 268:1965–75 (1993).

Kricka, L. in *Nonisotopic DNA Probe Techniques* (1992), Academic Press, San Diego, pp. 3–28.

Kubista, M. and Svanvik, N. "Probe for analysis of nucleic acids", WO 97/45539, Intl. Publ. Date Dec. 4, 1997.

Kuhn, H., Demidov, V., Nielsen, P. and Frank-Kamenetskii, M. "An experimental study of mechanism and specificity of peptide nucleic acid (PNA) binding to duplex DNA" Jour. Mol. Biol. 286:1337–45 (1999).

Kutyavin, I., Lukhtanov, E., Gamper, H. and Meyer, R. "Covalently linked oligonucleotide minor groove binder conjugates", WO 96/32496, Intl. Publ. Date Oct. 17, 1996.

Kyger, E., Krevolin, M. and Powell, M. "Detection of the hereditary hemochromatosis gene mutation by real-time fluorescence polymerase chain reaction and peptide nucleic acid clamping", Anal. Biochem. 260:142–48 (1998).

Lee, L., Connell, C., Woo, S., Cheng, R., McArdle, B., Fuller, C., Halloran, N. and Wilson, R. "DNA sequencing with dye-labeled terminators and T7 DNA polymerase: effect of dyes and dNTP on incorporation of dye-terminators and probability analysis of termination fragments", Nucleic Acids Res. 20:2471–83 (1992).

Lee, L., Spurgeon, S., Rosenblum, B. "Energy transfer dyes with enhanced fluorescence", U.S. Pat. No. 5,800,996, issued Sep. 1, 1998.

Lee, R., Kaushik, N., Modak, M., Vinayak, R. and Pandey, V. "Polyamide nucleic acid targeted to the primer binding site of the HIV-1 RNA genome blocks in vitro HIV-1 reverse transcription" Biochemistry 37:900–10 (1998).

Lee, L, Graham, R., Mullah, B. and Haxo, F. "Nitro-substituted non-fluorescent asymmetric cyanine dye compounds" U.S. patent application Ser. No. 09/012,525, filed Jan. 23, 1998.

Livak, K., Flood, S. and Marmaro, J. "Method for Detecting Nucleic Acid Amplification Using Self-Quenching Fluorescence Probe", U.S. Pat. No. 5,538,848, issued July 23, 1996.

Livak, K., Flood, S., Marmaro, J. and Mullah, K. "Self-quenching fluorescence probe", U.S. Pat. No. 5,723,591, issued Mar. 3, 1998.

Lutz, M. J., Benner, S. A., Hein, S., Breipohl, G. & Uhlmann, E. "Recognition of uncharged polyamide-linked nucleic acid analogs by DNA polymerases and reverse transcriptatses" J. Am. Chem. Soc. 119:3177–78 (1997).

Menchen, S., Lee, L., Connell, C., Hershey, N., Chakerian, V., Woo, S. and Fung, S. "4,7-Dichlorofluorescein dyes as molecular probes", U.S. Pat. No. 5,188,934, issued Feb. 23, 1993.

Meyer, R. "Incorporation of modified bases in oligonucleotides" in *Protocols for Oligoucleotide Conjugates,* Ed. S. Agrawal (1994) Humana Press, Totowa, N.J., pp. 73–92.

Misra, H., Pandey, P., Modak, M., Vinayak, R. and Pandey, V. "Polyamide nucleic acid-DNA chimera lacking the phosphate backbone are novel primers for polymerase reaction catalyzed by DNA polymerases" Biochemistry 37:1917–25 (1998).

Mullis, K. "Process for amplifying nucleic acid sequences", U.S. Pat. No. 4,683,202, issued Jul. 28, 1987.

Nielsen, P., Egholm, M., Berg, R. and Buchardt, O. "Sequence-selective recognition of DNA by strand displacement with a thymidine-substituted polyamide", Science 254:1497–1500 (1991).

Nielsen, P. "Peptide nucleic acid (PNA): A lead for gene therapeutic drugs", Antisense Therapeutics 4:76–84 (1996).

Rajur, S., Robles, J., Wiederholt, K., Kuimelis, R. and McLaughlin, L. "Hoechst 33258 tethered by a hexa (ethylene glycol) linker to the 5'-termini of oligodeoxynucleotide 15-mers: duplex stabilization and fluorescence properties", J. Organic Chem. 62:523–29 (1997).

Reeve, M. and Brown, T. "Reagents comprising chimeric molecules of nucleic acids and nucleic acid analogs" WO 95/08556, Intl. Publ. Date Mar. 30, 1995.

Ross, P., Lee, K. and Belgrader, P. "Discrimination of single-nucleotide polymorphisms in human DNA using peptide nucleic acid probes detected by MALDI-TOF mass spectrometry" Anal. Chem. 69:4197–4202 (1997).

Sanger, F., Nicklen, S. and Coulson, A. "DNA sequencing with chain-terminating inhibitors" Proc. Natl. Acad. Sci. USA 74:5463–5467 (1977).

Smith, L., Kaiser, R., Sanders, J. and Hood, L. "The synthesis and use of fluorescent oligonucleotides in DNA sequence analysis" Methods Enzymol. 155:260–301 (1987).

Smith, L., Hood, L., Hunkapiller, M., Hunkapiller, T., and Connell, C. "Automated DNA sequencing technique" U.S. Pat. No. 5,821,058, issued Oct. 13, 1998.

Stanton, T., Schindele, D., Renzoni, G., Pepich, B., Anderson, N., Clagett, J. and Opheim, K. "Preparation and use of monomeric phthalocyanine reagents" WO 8804777, Intl. Publ. Date: Jun. 30, 1988.

Syvanen, A., Aaalto-Setala, K., Harju, L., Kontula, K. and Soderlund, H. "A primer-guided nucleotide incorporation assay in the genotyping of apolipoprotein E" Genomics 8:684–92 (1990).

Tabor, S. and Richardson, C., J. Biol. Chem. 264:6447–58 (1989).

Uhlmann, E. "Peptide nucleic acids (PNA) and PNA-DNA chimera: from high binding affinity towards biological function" Biol Chem 379:1045–52 (1998).

Uhlmann, E., Will, D., Breipohl, G., Langner, D. and Ryte, A. "Synthesis and properties of PNA-DNA chimera" Angew. Chem., Intl. Ed. Eng. 35:2632–35 (1996).

Uhlmann, E., Breipohl, G., Benner, S., Lutz, M. "A nucleic acid amplification method using peptide nucleic acids as primers for thermostable DNA polymerases" EP 829542, Priority: Sept. 13, 1996.

Van der Laan, A., Brill, R., Kuimelis, R., Kuyl-Yeheskiely, E., van Boom, J., Andrus, A. and Vinayak, R. "A convenient automated solid-phase synthesis of PNA-(5')-DNA-(3')-PNA chimera", Tetrahedron Lett. 38:2249–52 (1997).

Van der Laan, A. C. et al. "Optimization of the binding properties of PNA-(5')-DNA Chimerae" Bioorg. Med. Chem. Lett. 8:663–68 (1998).

Vinayak, R., van der Laan, A., Brill, R., Otteson, K., Andrus, A., Kuyl-Yeheskiely, E. and van Boom, J. "Automated chemical synthesis of PNA-DNA chimera on a nucleic synthesizer", Nucleosides & Nucleotides 16:1653–56 (1997).

Vinayak, R. "Process and compounds for RNA synthesis", U.S. Pat. No. 5,281,701, issued Jan. 25, 1994.

Von Matt, P., De Mesmaeker, A., Pieles, U., Zurcher, W. & Altmann, K.-H. "2'-deoxyribo-PNAs: a structurally novel class of polyamide nucleic acids with good RNA and DNA binding affinity" Tetrahedron Lett. 40:2899–2902 (1999).

Wengel, J. "Oligonucleotide analogs", WO 99/14226, Intl. Publ. Date Mar. 25, 1999.

Will, D. W., Breipohl, G., Langner, D., Knolle, J. & Uhlmann, E. "The Synthesis of Polyamide Nucleic Acids using a Novel Monomethoxytrityl Protecting-Group Strategy" Tetrahedron 51:12069–12082 (1995).

We claim:

1. A method of producing a non-radioisotopically labelled chimeric extension product comprising the step of enzymatically extending a PNA-DNA chimera in the presence of a template nucleic acid, a polymerase and a primer extension reagent, wherein said primer extension reagent comprises a nucleotide 5'-triphosphate capable of effecting enzymatic chimera primer extension, the PNA-DNA chimera or the nucleotide 5'-triphosphate is labelled with a non-radioisotopic label selected from the group consisting of a fluorescent dye, a fluorescence quencher, a hybridization stabilizer, an energy-transfer dye pair, an electrophoretic mobility modifier, a chemiluminescent dye, an amino acid, a protein, a peptide, an enzyme, and an affinity ligand, and the PNA-DNA chimera has the structure:

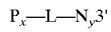

wherein:
each P is independently a PNA monomer;
x is an integer from 5 to 15;
L represents a covalent linkage between P and N;
each N is independently a nucleotide; and
y is an integer from 3 to 15;
with the proviso that the 3' terminal N has a 3' hydroxyl group.

2. The method of claim 1 in which the primer extension reagent comprises a mixture of nucleotide 5'-triphosphates capable of effecting continuous primer extension.

3. The method of claim 2 in which the mixture comprises four different nucleotide 5'-triphosphates, and further wherein
 a nucleotide 5'-triphosphate is ATP, dATP, 7-deaza dATP, 2-amino-ATP or 2-amino-dATP, and
 another nucleotide 5'-triphosphate is GTP, dGTP, or 7-deaza dGTP,
 another nucleotide 5'-triphosphate is CTP, dCTP, 5-methyl-CTP, 5-methyl-dCTP or 5-propynyl dCTP, and
 another nucleotide 5'-triphosphate is UTP, dUTP, dTTP, 5-Br-UTP, 5-Br-dUTP, 5-F-UTP, 5-F-dUTP or 5-propynyl-dUTP.

4. The method of claim 3 in which the mixture further includes a terminating nucleotide 5'-triphosphate.

5. The method of claim 1 in which the nucleotide 5'-triphosphate is a terminating nucleotide 5'-triphosphate.

6. The method of claim 4 or 5 in which the terminating nucleotide 5'-triphosphate is detectably labelled with a fluorescent dye.

7. The method of claim 1 in which the primer extension reagent further comprises a mixture of terminating nucleotide 5'-triphosphates.

8. The method of claim 7 in which the mixture comprises four different terminating nucleotide 5'-triphosphates, and further wherein
a terminating nucleotide 5'-triphosphate is ddATP, 7-deaza ddATP, or 2',3'-dideoxy-dehydro-ATP,
another terminating nucleotide 5'-triphosphate is ddGTP, 7-deaza ddGTP or 2',3'-dideoxy-dehydro-GTP,
another terminating nucleotide 5'-triphosphate is ddCTP or 2',3'-dideoxy-dehydro-CTP, and
another terminating nucleotide 5'-triphosphate is ddTTP, ddUTP, 2',3'-dideoxy-dehydro-TTP or 2',3'-dideoxy-dehydro-UTP.

9. The method of claim 8 wherein each different terminating nucleotide 5'-triphosphate is labelled with a different detectable label.

10. The method of claim 1 wherein $P_x$ is a 2-aminoethylglycine peptide nucleic acid.

11. The method of claim 1 in which each N is independently a 2'-deoxyribonucleotide.

12. The method of claim 1 in which each N is independently a ribonucleotide.

13. The method of claim 1 wherein the nucleobases of N are selected from the group consisting of C-5-alkyl pyrimidine, 2,6-diaminopurine, 2-thiopyrimidine, C-5-propyne pyrimidine, phenoxazine, 7-deazapurine, isocytidine, pseudo-isocytidine, isoguanosine, hypoxanthine, 8-oxopurine, and 4(3 H)-pyrimidone.

14. The method of claim 1 wherein the sugars of N are selected from the group consisting of 2'-O-alkyl-ribonucleotides, 2'-O-methyl-ribonucleotides, 2'-O-allyl-ribonucleotides, 2'-allyl ribonucleotides, 2'-halo-ribonucleotides, 2'-O-methoxyethyl-ribonucleotides, 4'-α-anomeric nucleotides, 1'-α-anomeric nucleotides, 2',4'-linked nucleotides, and bicyclic nucleotides.

15. The method of claim 1 wherein the PNA-DNA chimera is labelled at the amino terminus of the PNA moiety.

16. The method of claim 1 wherein the nucleotide 5'-triphosphate is labelled at the nucleobase.

17. The method of claim 16 wherein the nucleobase label sites are the N-9 or C-8 positions of the purine or deazapurine, and the C-5 position of the pyrimidine.

18. The method of claim 1 where the fluorescent dyes are selected from the group consisting of FAM, TET, HEX, JOE, TAMRA, d-TAMRA, JODA, ROX, VIC, NED, dJON, dR139, 4,7-dichloro-fluoresceins, 4,7-dichloro-rhodamines, and cyanines.

19. The method of claim 1 where the fluorescence quenchers are selected from the group consisting of TAMRA, d-TAMRA, ROX, DABCYL, DABSYL, malachite green, NTB, and cyanines.

20. The method of claim 1 where the hybridization-stabilizers are minor groove binders.

21. The method of claim 1 where the minor groove binders are selected from the group consisting of Hoechst 33258, $CDPI_{1-3}$, MGB1, netropsin, and distamycin.

22. The method of claim 1 where the affinity ligands are selected from the group consisting of biotin, 2,4-dinitrophenyl, digoxigenin, cholesterol, polyethyleneoxy, peptides, and fluorescein.

23. The method of claim 1 wherein L is selected from the group consisting of a covalent bond, alkyldiyl consisting of 1–20 carbon atoms, aryldiyl, O linker, and $-(CH_2CH_2O)_m-$ where m is 1 to 6.

24. The method of claim 1 in which the template nucleic acid is a DNA and the polymerase is selected from the group consisting of Klenow, T4, Bst, AmpliTaq, AmpliTaq Gold, AmpliTaq Stoffel fragment, Sequenase, Vent, Pfu, and bacteriophage T7.

25. The method of claim 1 in which the template nucleic acid is an RNA and the polymerase is a reverse transcriptase.

26. The method of claim 1 in which the template nucleic acid is a metaphase or interphase chromosome.

27. The method of claim 26 in which the chromosome is denatured.

28. The method of claim 1 in which the PNA-DNA chimera is immobilized on a solid substrate.

29. The method of claim 28 in which the chimera is covalently attached to the solid substrate, optionally with the aid of a linker.

30. The method of claim 1 in which the template nucleic acid is immobilized on a solid substrate.

31. The method of claim 30 in which the template nucleic acid is covalently attached to the solid substrate, optionally with the aid of a linker.

32. The method of claim 28 or 30 wherein the solid substrate is selected from the group consisting of polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of any of the above solid substrates.

33. The method of claim 28 or 30 wherein the solid substrate is selected from the group consisting of small particles, beads, membranes, frits, slides, plates, micromachined chips, alkanethiol-gold layers, non-porous surfaces, and polynucleotide- immobilizing media.

34. A kit for primer extension comprising:
a PNA-DNA chimera primer, said primer comprising 5 to 15 contiguous PNA monomer units, 3 to 15 contiguous nucleotides, and a 3' hydroxyl terminus; one or more nucleotide 5'-triphosphates and; a polymerase enzyme,
wherein the chimera primer or a nucleotide 5'-triphosphate is non-radioisotopically labelled.

35. The kit of claim 34 further comprising a template nucleic acid comprising a sequence complementary to the chimera primer or containing one or more mismatches to the chimera primer.

36. A method of sequencing a template nucleic acid, comprising the steps of:
a) generating a labelled primer extension product by enzymatically extending a primer-template nucleic acid hybrid in the presence of a polymerase and a terminating nucleotide 5'-triphosphate, wherein said primer is a PNA-DNA chimera and either said primer or said terminating nucleotide 5'-triphosphate is detectably and non-radioisotopically labelled with a non-radioisotopic label selected from the group consisting of a fluorescent dye, a fluorescence quencher, a hybridization stabilizer, an energy-transfer dye pair, an electrophoretic mobility modifier, a chemiluminescent dye, an amino acid, a protein, a peptide, an enzyme, and an affinity ligand, and the PNA-DNA chimera has the structure:

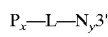

wherein:
each P is independently a PNA monomer;
x is an integer from 5 to 15;
L represents a covalent linkage between P and N;

each N is independently a nucleotide; and
y is an integer from 3 to 15;
with the proviso that the 3' terminal N has a 3' hydroxyl group;

b) separating the labelled primer extension products based on size; and c) determining the sequence of the template nucleic acid.

37. The method of claim 36 wherein a nested set of labelled primer extension products are generated by a mixture of enzymatically extendable nucleotide 5'-triphosphates capable of supporting continuous primer extension.

38. The method of claim 36 wherein the PNA-DNA chimera is labelled.

39. The method of claim 36 wherein the terminating nucleotide 5'-triphosphate is labelled.

40. The method of claim 39 wherein the labelled, terminating nucleotide 5'-triphosphate is selected from the group consisting of a labelled ddNTP, a labelled 2'-amino, 2'-deoxynucleotide, a labelled 2'-halo, 2'-deoxynucleotide, and a labelled 2',3'-dideoxy-dehydronucleotide.

41. A method of reverse transcription comprising the step of generating labelled primer extension products by enzymatically extending a primer-template RNA hybrid in the presence of a reverse transcriptase, a mixture of enzymatically-extendable nucleotide 5'-triphosphates capable of supporting continuous primer extension, wherein said primer is a PNA-DNA chimera and either said primer or a nucleotide 5'-triphosphate is non-radioisotopically labelled with a non-radioisotopic label selected from the group consisting of a fluorescent dye, a fluorescence quencher, a hybridization stabilizer, an energy-transfer dye pair, an electrophoretic mobility modifier, a chemiluminescent dye, an amino acid, a protein, a peptide, an enzyme, and an affinity ligand, and
the PNA-DNA chimera has the structure:

$$P_x—L—N_y3'$$

wherein:
each P is independently a PNA monomer;
x is an integer from 5 to 15;
L represents a covalent linkage between P and N;
each N is independently a nucleotide; and
y is an integer from 3 to 15;
with the proviso that the 3' terminal N has a 3' hydroxyl group.

42. A method of DNA amplification comprising the steps of:

a) generating labelled amplification products by enzymatically extending a primer-template nucleic acid hybrid in the presence of two primers each of which is capable of hybridizing to the template and wherein one or both of which is a PNA-DNA chimera primer, a DNA polymerase and a mixture of enzymatically-extendable nucleotide 5'-triphosphates capable of supporting continuous primer extension, wherein either said primers or nucleotide 5'-triphosphates are non-radioisotopically labelled with a non-radioisotopic label selected from the group consisting of a fluorescent dye, a fluorescence quencher, a hybridization stabilizer, an energy-transfer dye pair, an electrophoretic mobility modifier, a chemiluminescent dye, an amino acid, a protein, a peptide, an enzyme, and an affinity ligand, and
the PNA-DNA chimera has the structure:

$$P_x—L—N_y3'$$

wherein:
each P is independently a PNA monomer;
x is an integer from 5 to 15;
L represents a covalent linkage between P and N;
each N is independently a nucleotide; and
y is an integer from 3 to 15;
with the proviso that the 3' terminal N has a 3' hydroxyl group; and b) cycling the temperature to effect denaturation, annealing, and primer extension to form an amplification product by extension of the primers with nucleotide 5'-triphosphates;
wherein one or both of the 5' terminii of the amplification product bears the PNA sequence of the chimera primers.

43. The method of claim 42 in which the amplification product is immobilized by hybridization on a solid substrate comprising a nucleic acid with a sequence complementary to the PNA sequence of the amplification product.

* * * * *

SEQUENCE LISTING

```
<160> NUMBER OF SEQ ID NOS: 19

<210> SEQ ID NO 1
<211> LENGTH: 6
<212> TYPE: DNA
<213> ORGANISM: Unknown Organism
<220> FEATURE:
<223> OTHER INFORMATION: Description of Unknown Organism: Bacterial

<400> SEQUENCE: 1 tagttc                                                               6

<210> SEQ ID NO 2
```

-continued

```
<211> LENGTH: 7
<212> TYPE: DNA
<213> ORGANISM: Unknown Organism
<220> FEATURE:
<223> OTHER INFORMATION: Description of Unknown Organism: Bacterial

<400> SEQUENCE: 2 tagttct                                                              7

<210> SEQ ID NO 3
<211> LENGTH: 8
<212> TYPE: DNA
<213> ORGANISM: Unknown Organism
<220> FEATURE:
<223> OTHER INFORMATION: Description of Unknown Organism: Bacterial

<400> SEQUENCE: 3 tagttcta                                                             8

<210> SEQ ID NO 4
<211> LENGTH: 9
<212> TYPE: DNA
<213> ORGANISM: Unknown Organism
<220> FEATURE:
<223> OTHER INFORMATION: Description of Unknown Organism: Bacterial

<400> SEQUENCE: 4 tagttctag                                                            9

<210> SEQ ID NO 5
<211> LENGTH: 10
<212> TYPE: DNA
<213> ORGANISM: Unknown Organism
<220> FEATURE:
<223> OTHER INFORMATION: Description of Unknown Organism: Bacterial

<400> SEQUENCE: 5
tagttctaga                                                          10

<210> SEQ ID NO 6
<211> LENGTH: 6
<212> TYPE: DNA
<213> ORGANISM: Unknown Organism
<220> FEATURE:
<223> OTHER INFORMATION: Description of Unknown Organism: Bacterial

<400> SEQUENCE: 6 tagttc                                                               6

<210> SEQ ID NO 7
<211> LENGTH: 9
<212> TYPE: DNA
<213> ORGANISM: Unknown Organism
<220> FEATURE:
<223> OTHER INFORMATION: Description of Unknown Organism: Bacterial

<400> SEQUENCE: 7 tagttctag                                                            9

<210> SEQ ID NO 8
<211> LENGTH: 38
<212> TYPE: DNA
<213> ORGANISM: Unknown Organism
<220> FEATURE:
<223> OTHER INFORMATION: Description of Unknown Organism: Bacterial

<400> SEQUENCE: 8
```

```
aaggtccgaa tcaagatctg gtacgataca caactcgc                              38

<210> SEQ ID NO 9
<211> LENGTH: 11
<212> TYPE: DNA
<213> ORGANISM: Unknown Organism
<220> FEATURE:
<223> OTHER INFORMATION: Description of Unknown Organism: Bacterial

<400> SEQUENCE: 9
actagttcta g                                                           11

<210> SEQ ID NO 10
<211> LENGTH: 12
<212> TYPE: DNA
<213> ORGANISM: Unknown Organism
<220> FEATURE:
<223> OTHER INFORMATION: Description of Unknown Organism: Bacterial

<400> SEQUENCE: 10
actagttcta ga                                                          12

<210> SEQ ID NO 11
<211> LENGTH: 13
<212> TYPE: DNA
<213> ORGANISM: Unknown Organism
<220> FEATURE:
<223> OTHER INFORMATION: Description of Unknown Organism: Bacterial

<400> SEQUENCE: 11
actagttcta gac                                                         13

<210> SEQ ID NO 12
<211> LENGTH: 38
<212> TYPE: DNA
<213> ORGANISM: Unknown Organism
<220> FEATURE:
<223> OTHER INFORMATION: Description of Unknown Organism: Bacterial

<400> SEQUENCE: 12
aaggtccgaa tcaagacctg gtacgataca caactcgc                              38

<210> SEQ ID NO 13
<211> LENGTH: 38
<212> TYPE: DNA
<213> ORGANISM: Unknown Organism
<220> FEATURE:
<223> OTHER INFORMATION: Description of Unknown Organism: Bacterial

<400> SEQUENCE: 13
aaggtccgaa tcaagatccg gtacgataca caactcgc                              38

<210> SEQ ID NO 14
<211> LENGTH: 17
<212> TYPE: DNA
<213> ORGANISM: Mouse Murine Xist gene

<400> SEQUENCE: 14
actaggtccc ggcttta                                                     17

<210> SEQ ID NO 15
<211> LENGTH: 14
<212> TYPE: DNA
<213> ORGANISM: Mouse Murine Xist gene
```

-continued

```
<400> SEQUENCE: 15
actaggtccc ggct                                                          14

<210> SEQ ID NO 16
<211> LENGTH: 20
<212> TYPE: DNA
<213> ORGANISM: Mouse Murine Xist gene

<400> SEQUENCE: 16
aacagttagg tcccggcttt                                                    20

<210> SEQ ID NO 17
<211> LENGTH: 20
<212> TYPE: DNA
<213> ORGANISM: Mouse Murine Xist gene

<400> SEQUENCE: 17
actgggatgc aaagagcatt                                                    20

<210> SEQ ID NO 18
<211> LENGTH: 20
<212> TYPE: DNA
<213> ORGANISM: Mouse Murine Xist gene

<400> SEQUENCE: 18
tgcctgggat aaaagcaaag                                                    20

<210> SEQ ID NO 19
<211> LENGTH: 14
<212> TYPE: DNA
<213> ORGANISM: Unknown Organism
<220> FEATURE:
<223> OTHER INFORMATION: Description of Unknown Organism:  Bacterial

<400> SEQUENCE: 19
acacgacggc cagt                                                          14
```